(12) United States Patent
Griffin et al.

(10) Patent No.: US 9,909,154 B2
(45) Date of Patent: Mar. 6, 2018

(54) METHODS FOR PRODUCING DICARBOXYLIC ACIDS

(71) Applicant: Synthetic Genomics, Inc., La Jolla, CA (US)

(72) Inventors: Benjamin M. Griffin, San Diego, CA (US); Spiros Kambourakis, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/548,880

(22) Filed: Nov. 20, 2014

(65) Prior Publication Data

US 2015/0176041 A1    Jun. 25, 2015

Related U.S. Application Data

(60) Provisional application No. 61/906,819, filed on Nov. 20, 2013.

(51) Int. Cl.
C12P 7/64       (2006.01)
C12N 9/02       (2006.01)

(52) U.S. Cl.
CPC ............ *C12P 7/6409* (2013.01); *C12N 9/001* (2013.01); *C12N 9/0071* (2013.01); *C12Y 114/14001* (2013.01)

(58) Field of Classification Search
None
See application file for complete search history.

(56) References Cited

U.S. PATENT DOCUMENTS

2013/0267012 A1   10/2013   Steen et al.
2013/0309733 A1   11/2013   Pang et al.

OTHER PUBLICATIONS

L.O. Narhi et al. "Characterization of a Catalytically Self-Sufficient 119,000 Dalton Cytochrom P-450 Monooxygenase induced by Barbiturates in Bacillus megaterium", J. Biol. Chem. 261(16):7160-7169 (1986).*
Choi et al.: "Cloning, expression and characterization of CYP102D1, a self-sufficient P450 monooxygenase from Streptornyces avermitilis"; FEBS Journal 279, 2012, p. 1650-1662.
Cryle et al.: "Carbon-carbon bond cleavage by cytochrome $P450_{Biol}$ (CYP107H1)";. Chem Commun (Camb). 2004, (1);86-7.
Cryle et al.:. "Facile determination of the absolute stereochemistry of hydroxy fatty acids by GC application to the analysis of fatty acid oxidation by a $P450_{BM3}$ mutant"; Tetrahedron Assymetry, 2007, 18(4), p. 547-551.
Cryle et al.: "Structural insights from a P450 Carrier Protein complex reveal how specificity is achieved in the $P450_{Biol}$ ACP complex"; PNAS, Oct. 14, 2008, v. 105:41, p. 15696-15701.
English et al.: "Induction of cytochrome $P_{-3}$ (CYP 102) by non-steroidal anti-inflammatory drugs in Bacillus megaterium"; Biochem. J., 1996:316, p. 279-283.
Hannemann, Frank et al.: "Cytochrome P450 systems—biological variations of electron transport chains"; Biochim Biophys Acta,. Mar. 2007, 1770(3), p. 330-344.
PubChem, Compound Summary for CID 985. Palmitic acid Sep. 16, 2004 [Retrieved from the Internet May 4, 2014: <http://pubchem.ncbi.nlm.nih.gov/summary/summary.cdi?from=compound&cid=985>); p. 1.
PubChem. Compound Summary for CID 10458. Trldecanedioic acid Mar. 26, 2005; [Retrieved from the Internet May 4, 2014: <http://pubchem.ncbi.nlm.nih.gov/summary/summary.cgi?from=comPound&cid=10458>), p. 1.
PubChem. Compound Summary for CID 10459. Hexadecanedioic acid. Mar. 26, 2005 [Retrieved from the Internet May 4, 2014: <http://pubchem.ncbi.nlm.nih.gov/summary/summary.cgi?from=compound&cid=10459>]; p. 1.
international Search Report issued on Jun. 5, 2015 regarding PCT/US2014/066595.
Oliver, C.F.et al.: "A Single Mutation in Cytochrome P450 BM3 Changes Substrate Orientation in a Catalytic Intermediate and the Regiospecificity of Hydroxylation": Biochemistry, vol. 36, No. 7, Feb. 1, 1997, pp. 1567-1572.
Schumacher, J.D. et al.: "Degradation of alicyclic molecules by Rhodococcus ruber CD4", Applied Microbiology and Biotechnology, vol. 52, 1999, pp. 85-90.
Supplementary Partial European Search Report dated Jul. 17, 2017, regarding EP 14 86 3233.
Warburton, E.J.: *The Metabolism of Cycloalkanes by Different Species of Xanthobacter*; Database Dissabs [Online],1989, database accession No. 89:34269, XP002771397.

* cited by examiner

*Primary Examiner* — Rebecca E Prouty
(74) *Attorney, Agent, or Firm* — DLA Piper LLP (US)

(57) ABSTRACT

The present invention provides methods of producing dicarboxylic acids. The methods involve incubating a fatty acid or hydrocarbon substrate with an enzyme to produce a dicarboxylic acid product. The enzyme acts on the substrate to produce a product that has been both over-oxidized and has undergone cleavage of a C—C bond. In some embodiments the enzymes having these useful characteristics are mutants of a cytochrome P450 enzyme, for example an enzyme of the class CYP102 or a mutant thereof. The invention provides enzymes where these desirable characteristics can be found in a single enzyme, and thus in some embodiments the methods can be performed through the action of a single enzyme.

15 Claims, 18 Drawing Sheets

| | 0018 | 2875 | yetO-WT |
|---|---|---|---|
| 4779 | 61 | 58 | 60 |
| 0018-*Bacillus* | | 59 | 74 |
| 2875-*Bacillus* | | | 60 |

FIG. 3

| Plasmid | Mutant | [p450,µM] nmole/mL[1] | $U^2$/nmole Lauric[1] | $U^2$/nmole Myristic | $U^2$/nmole Palmitic | % P450 (g/g) in Lysate |
|---|---|---|---|---|---|---|
| pSGI-040 | yetO-wt | 8.0 | 2920 | 2970 | 606 | 10 |
| pSGI-055 | yetO-F89A | 3.9 | 445 | 144 | - | 11.9 |
| pSGI-058 | yetO-F89V | 3.5 | 994 | 540 | 166 | 9.1 |
| pSGI-056 | yetO-F89I | 4.0 | 882 | 228 | 109 | 9.6 |
| pSGI-057 | yetO-F89S | 3.3 | 569 | 178 | 80 | 9.5 |
| pSGI-118 | BM3-wt | 3.1 | 749 | NM[3] | 653 | ~20[4] |
| pSGI-004 | BM3-F87A[1] | 14.5 | 110 | 303 | 344 | 19 |

FIG. 4A

METHODS FOR PRODUCING DICARBOXYLIC ACIDS

This application claims the benefit of U.S. provisional application Ser. No. 61/906,819, filed Nov. 20, 2013, which is hereby incorporated by reference in its entirety, including all Tables, Figures, and claims.

FIELD OF THE INVENTION

The invention relates to the enzymatic production of dicarboxylic acids from hydrocarbons or fatty acids.

INCORPORATION OF SEQUENCE LISTING

The materials in the accompanying Sequence Listing is hereby incorporated by reference into this application. The accompanying sequence listing text file, name SGI1760_1_Sequence Listing_ST25, was created on Nov. 18, 2014 and is 53 KB. The file can be assessed using Microsoft Word on a computer that uses Windows OS.

BACKGROUND

Long chain di-carboxylic acids are versatile chemical intermediates that are used in the synthesis of perfumes, polymers, adhesives and lubricants, as well as by the pharmaceutical industry for the synthesis of antibiotics. Diacids with carbon chains longer than C10-C12 carbons, offer potential advantages over shorter diacids but current methods of synthesis of these compounds is commercially inadequate. One of the most important uses of such compounds is in the synthesis of polymers. In these uses long-chain di-carboxylic acids provide greater flexibility and strength than is available with short-chain di-carboxylic acids due to their ability to bend, which minimizes breakage and reduces the number of links in a polymers.

Current methods for the synthesis of long chain dicarboxylic acids involve either the chemical oxidation of unsaturated fatty acids, or the enzymatic oxidation of alkanes or fatty acids using whole cell fermentations (Huf, S. et al. *Eur. J Lipid Sci. Technol.* (2011), 113: 548-561). Chemical methods for the synthesis of dicarboxylic acids require derivatized fatty acids, such as unsaturated fatty acids (e.g., oleic, palmitoleic), hydroxylated fatty acids (e.g., ricinoleic acid), and the like. Typical chemistries that are used for these transformations include ozonolysis, which oxidizes an alkene to two carboxylic acids. Because ozonolysis is expensive and difficult to practice at the industrial scale, other chemical methods for the oxidation of unsaturated fatty acid have been developed. But these methods often suffer from lower yields (Warwel S, et al *Lipid Technol* 1997, 9:10-14). Various methods developed for the synthesis of dicarboxylic acids from fatty acids are described in Metzger, J. O., *Eur. J. Lipid Sci. Technol.* 2009, 111, 865-876. Other chemical methods such as cross metathesis technologies have been reported, but are not currently used in the commercial manufacturing of long fatty acids.

Some biocatalytic approaches for the synthesis of large (>C12) di-carboxylic acids utilize omega hydroxylase in the P450 family. These approaches utilize yeasts such as *Candida*, which oxidize the alpha and omega positions saturated wax hydrocarbons such as tridecane to tridecanedioic acid (Shuchen, L; et al *Enz. Microb. Technol.* 2004, 34, 73; Liu, S C; et al *Pertochem Technol.* 2002, 31, 558). But these methods rely on the use of non-renewable petrochemical waxes and require complicated fermentations of engineered bacteria with limited titers yields and productivities (Huf, S. et al *Eur. J Lipid Sci. Technol.* 2011, 113, 548). These methods also are limited to di-carboxylic acids having the same number of carbons as the starting wax or fatty acid. (Huf, S et al *Eur. J Lipid Sci. Technol.* (2011), 113, 548-561).

The P450 enzyme CYP107H1 (BioI) oxidizes fatty acids with C12 to C16 carbons to produce a single product, pimelic acid (heptanedioic acid C7). Besides being very selective for its products, CYP107H1 requires acyl-carrier-protein (ACP)-bound fatty acid as substrate. When free fatty acids are used as substrates, CYP107H1 gives a number of mono-hydroxylation products. Another disadvantage of this enzyme is the requirement for two additional enzymes, a ferredoxin and a feredoxin reductase, that decrease the activity and catalytic turnover of the enzyme (Lawson, R. J et al *Biochemistry* 2004, 43, 12390; Cryle, M J, Schlichting I. *PNAS*, 2008, 105, 15696).

It would be useful to have enzymes that could produce dicarboxylic acid products by over-oxidation of the substrates and also perform cleavage of the C—C bonds. This would be particularly useful if it could be done with a single enzyme, and from renewable resources such as fatty acids.

SUMMARY

The present invention provides methods and compositions for producing dicarboxylic acids. The methods involve contacting a fatty acid or hydrocarbon substrate with one or more enzymes to produce a dicarboxylic acid product. The one or more enzymes act on the substrate to produce a product that has been both over-oxidized and has undergone cleavage of a C—C bond. In some embodiments the one or more enzymes having these useful properties are mutants of a cytochrome P450 enzyme, for example a mutant an enzyme of the class CYP102 (cytochrome P450BM-3). The invention provides enzymes where these desirable characteristics can be found in a single enzyme, and thus in some embodiments the methods can be performed through the action of a single enzyme.

In a first aspect the invention provides a method of producing a dicarboxylic acid. The method involves contacting a hydrocarbon or fatty acid substrate with an enzyme that oxidizes the hydrocarbon or fatty acid substrate and breaks a C—C bond of the hydrocarbon or fatty acid substrate to produce a dicarboxylic acid product. In one embodiment the substrate is a fatty acid, which can be a saturated or unsaturated fatty acid. In various embodiments the saturated fatty acid can have an aliphatic chain of 4-28 carbon atoms, or an aliphatic chain of 15-20 carbon atoms.

In other embodiments the substrate is a hydrocarbon, for example a cyclic hydrocarbon. In some particular embodiments the cyclic hydrocarbon can be cyclooctane or cyclodecane, or can be selected from the group consisting of cyclohexane, cyclohexanol, cyclooctane, and cyclodecane.

In one embodiment of the invention the dicarboxylic acid product has a smaller number of carbons than the fatty acid substrate, for example the dicarboxylic acid product can have 3 carbons fewer than the fatty acid substrate. Hydroxylated fatty acid products can be produced in addition to the dicarboxylic acid product when the enzyme is incubated with the fatty acid. In some embodiments the enzyme is a CYP102 family enzyme. In some of these embodiments the enzyme can have between 55% and 99% amino acid sequence identity with BM3 (CYP102A1). The enzyme can be BM3-F87A.

In some embodiments the substrate is a fatty acid and the enzyme over-oxidizes the fatty acid. The reaction can involve the over-oxidation of adjacent diols. Oxidizing the fatty acid and breaking the C—C bond can comprise the reaction mechanism:

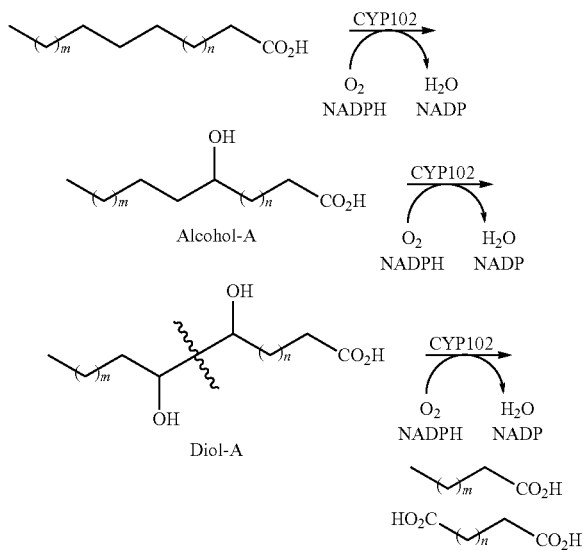

wherein m+n=14-20. In some embodiments m and n are positive integers between 4 and 7 and m+n=9-14, and in some specific embodiments the substrate is tridecanedioic acid (C19) and the dicarboxylic acid is palmitic acid (C16); or the substrate is cyclodecane and the dicarboxylic acid is sebacic acid (C7).

In some embodiments of the invention the substrate is a hydrocarbon and is incubated with the enzyme in a cell free reaction. The enzyme can be immobilized on a solid support. The enzyme can have at least 50% sequence identity to CYP102A1 wt (BM3) or CYP102A2 wt (YetO) or CYP102A3 wt (yrhJ) enzymes, and/or the enzyme can have at least one amino acid residue different from CYP102A1 wt (BM3) and/or CYP102A2 wt (YetO) and/or CYP102A3 wt (yrhJ) enzymes. In other embodiments the enzyme has at least 50% sequence identity to CYP102A1 wt (BM3) or CYP102A2 wt (YetO) and has at least one amino acid residue different from CYP102A1 wt (BM3) and/or CYP102A2 wt (YetO). And in more embodiments the enzyme is selected from the group consisting of: BM3 (F87A), YetO (F89A), YetO (F89I), YetO (F89S), YetO (F89V).

These and other objects, aspects, and features of the invention will become more fully apparent to those of ordinary skill in the art upon review of the following detailed description of the invention and the claims in conjunction with the accompanying figures.

DESCRIPTION OF THE DRAWINGS

FIG. 3 is a table showing the pairwise percent identity of selected wild type BM3 homologs.

FIG. 4a is a table showing the activities of BM3-wt, YetO-wt and selected mutant enzymes on various fatty acids. Legend: 1: Avg of two different growths; 2: Unit definition: 1U=1 nmole of NADPH consumed per min; 3: NM: not measured; 4: This concentration was not measured in this experiment, however it was shown elsewhere that BM3 and its mutant F87A express about the same.

DETAILED DESCRIPTION OF THE INVENTION

Figure 1:
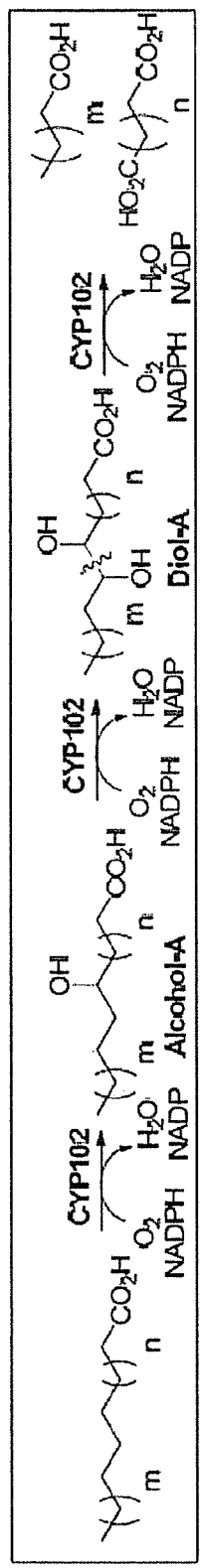
FIG. 1 is a pathway showing the oxidation of fatty acids by a P450 enzyme (CYP102) to produce a dicarboxylic acid product.

The present invention provides methods of oxidizing fatty acid or hydrocarbon substrates to produce dicarboxylic acid products. The methods are performed through the use of enzymes that have the ability to over-oxidize the fatty acid or hydrocarbon substrates and additionally to cleave a C—C bond of the substrate, resulting in a dicarboxylic acid product. The enzymes can be Cytochrome P450 enzymes that are members of the CYP102 sub-family, and homologs thereof. These enzymes are hemoproteins that catalyze the monooxygenation of various substrates.

The present methods offer several advantages. The present methods can be carried out without the need to utilize toxic chemicals, which are often required in chemical processes for the oxidation of fatty acids or hydrocarbons. The present methods also offer a substantial reduction in the costs of materials involved, as well as higher reaction product yields than have previously been available. Furthermore, the present methods can be performed using a much wider selection of starting materials, such as derivatized, un-derivatized, saturated or unsaturated fatty acids, in addition to hydrocarbons. Yet another advantage offered by the present invention is a much wider class of dicarboxylic acids that can be produced. The invention allows the production not only of dicarboxylic acid products having the same number of carbons as the chain of the starting fatty acid or other hydrocarbons, but also of dicarboxylic acid products having a smaller number of carbons as the chain of the starting fatty acid or hydrocarbon. The present methods can also accomplish the synthesis of dicarboxylic acids using a wider class of petroleum-derived hydrocarbons as substrates, for example, cyclic hydrocarbons (e.g., cyclooctane, cyclodecane, etc.) or aliphatic hydrocarbons. Furthermore, the present methods can be performed using a single enzyme that acts on the hydrocarbon substrate or a product of the reaction of the enzyme on the hydrocarbon substrate. The enzymes of the present invention can perform the initial derivatization of the hydrocarbon as well as the subsequent oxidation and breaking of the C—C bond to arrive at the dicarboxylic acid product of the method. In some embodiments the enzyme acts on a fatty acid substrate and produces a dicarboxylic acid product.

In various embodiments the methods of the invention can further involve one or more steps of converting intermediates or side products of the reactions and/or dicarboxylic acid products of the reaction into other desirable products. For example, various compositions containing diols, vicinal diols, and alcohols (e.g., keto alcohols) can be produced either as intermediates or as reaction side products. The conversion of these intermediates or side products into other desirable products further drives the reaction forward and increases yields compared to methods that do not utilize these one or more steps. Another step that can be included in any of the methods of the invention is the purification of dicarboxylic acids from the reaction products. This purification step can involve the normal processes used to purify dicarboxylic acids, such as by chromatographic methods. Persons of ordinary skill in the art with resort to this disclosure will realize that the specific methods of purifying the dicarboxylic acids will depend on the dicarboxylic acid to be purified or isolated and the contaminants to be eliminated. In some embodiments the purification can involve one or more steps of extracting with diethyl ether (or another organic and/or polar solvent), drying, and fractionally distilling the dicarboxylic acid product. Other methods known to those of skill in the art can also be utilized. In various embodiments the step of purifying the dicarboxylic acid can involve purifying by at least 50% w/w or at least 75% w/w or at least 85% w/w or at least 95% w/w.

In other embodiments the methods of the invention also involve a step of polymerizing the dicarboxylic acid products. The dicarboxylic acids can be polymerized to form polymerized products or intermediates, e.g. for the synthesis of other molecules. In some embodiments the dicarboxylic acids are polymerized to form nylons or precursors for synthesizing nylons. The step of polymerizing the dicarboxylic acid can be polymerizing at least 25% or at least 50% or at least 75% of the dicarboxylic acid product. Polymerization the dicarboxylic acid can mean polymerizing only the dicarboxylic acid product or polymerizing the dicarboxylic acid with another molecule in the mixture. In another embodiment the method can include a step of adding another molecule to the mixture and polymerizing the dicarboxylic acid with the molecule added to the mixture. The method can further involve a step of adding a molecule to initiate or enable polymerization of the dicarboxylic acid product.

The methods of the invention can also involve one or more steps of a) converting dicarboxylic acids to other desirable chemical products, or b) purifying dicarboxylic acids or c) polymerizing dicarboxylic acids, or each of steps a), b), and c), depending on the specific objectives involved.

Reaction Scheme

The methods involve producing a dicarboxylic acid from a hydrocarbon or fatty acid starting material by contacting the hydrocarbon or fatty acid with one or more enzymes that oxidize the hydrocarbon or fatty acid and break a C—C of the hydrocarbon or fatty acid and produce a dicarboxylic acid product. The contacting can be done by combining the reactants in a solution or reaction mixture. The reactants can be incubated or left in contact for an appropriate period of time.

The inventors discovered unexpectedly that certain enzymes have the ability to over-oxidize hydrocarbons and fatty acid substrates and break a C—C bond of the substrate to produce the dicarboxylic acid product. In various embodiments the enzymes are members of the CYP102 subfamily of enzymes. Various forms of the enzyme and mutants or homologs of the enzymes were discovered to have this ability. By over-oxidizing the hydrocarbon or fatty acid substrate it is possible to first oxidize the substrate and then further oxidize to cleave the C—C bond to produce a dicarboxylic acid molecule. By "over-oxidize" is meant that the enzyme reaction performs at least 3 oxidations on the molecule. The three oxidations can be, for example, the oxidations of two carbons to hydroxyls and a third oxidation of either the production of a carbonyl or the cleavage of a C—C bond. The cleavage of a C—C bond can produce a dicarboxylic acid. In some embodiments the enzyme over-oxidizes and performs at least 4 oxidations on the substrate molecule. Thus, oxidation can be the formation of a hydroxyl, or the formation of a ketone, or the breaking of a C—C bond. Each of these oxidations can be performed on atoms or groups of atoms attached to the backbone chain of the hydrocarbon molecule. In one embodiment the methods are carried out using a single enzyme that acts on the substrate to produce the dicarboxylic acid reaction product, thus facilitating large scale production of the dicarboxylic acids. The enzyme can also be a soluble enzyme. In one embodiment the enzyme oxidizes adjacent diols on the hydrocarbon or fatty acid substrate. As an example, FIG. 1 (also below) depicts a reaction scheme of the method of the invention, and the diol-A species exhibits adjacent diols, which are further oxidized in the pathway to form a breakage of the C—C bond and result in the production of a dicarboxylic acid and a fatty acid. Breaking a C—C bond means breaking a covalent bond to separate a molecule into separate molecules thus, for example, causing a double bond to change to a single bond is not considered to break a C—C bond as used herein. But to break a palmitic acid (C16) molecule into a tridecanoic acid (C13) and a three carbon molecule (e.g., propanoic acid) is to break a C—C bond.

Thus, in some embodiments the methods utilize a reaction of the mechanism (I):

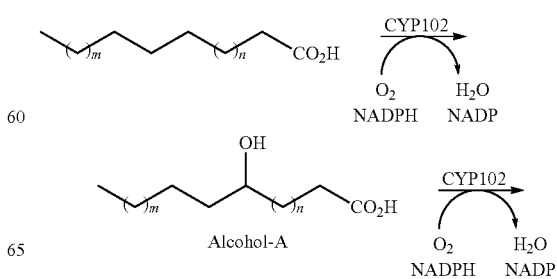

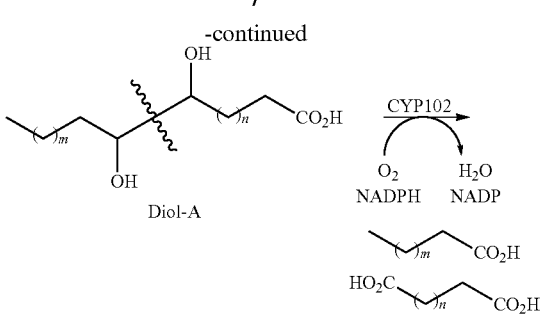

Diol-A where m and n are positive integers. In various embodiments m+n=9 or 10 or 11 or 12 or 13 or 14 or 15 or 16 or 17 or 18 or 19 or 20 or 6-11 or 6-16 or 9-14 or 9-20 or 14-20. In some embodiments m and n are each any of 0 or 1 or 2 or 3 or 4 or 5 or 6 or 7 or 8 or 9 or 10 or 11 or 12 or 13 or 14 or 15 or 16 or 17 or 18 or 19 or 20 or 0-9, or 4-7 or 4-10 or 6-16 or 10 or 11 or 12 or 13 or 14 or 0-14 or 12-14. In some embodiments n is 9-14 and m is 0-5; or n can be 12-17 and m is 0.

In some embodiments the reactions of the invention produce mixtures of alcohols and diols. In various embodiments the reactions have greater than 90% selectivity for producing the carbon chain length of the dicarboxylic acid formed from the over-oxidation of the hydrocarbon or fatty acid substrates, meaning that greater than 90% of the dicarboxylic acids produced are of a particular chain length. One or more of the dicarboxylic acids produced by the methods of the invention can have three fewer carbon atoms (in the chain) compared to the hydrocarbon or fatty acid substrate. Thus, in various embodiments the fatty acid palmitic acid (C16) can be used as a substrate to produce tridecanedioic acid (C13) as a major dicarboxylic acid product with at least 90% selectivity or at least 80% selectivity or at least 75% selectivity or at least 60% selectivity or at least 50% selectivity. Selectivity refers to the molar ratio of the product formed. But in other embodiments the fatty acid product can also have two fewer or four fewer or five fewer carbon atoms in its chain compared to the carbon chain of the hydrocarbon or fatty acid substrate, and the product can also be a mixture of fatty acids of two fewer or three fewer or four fewer or five fewer carbon atoms compared to the hydrocarbon or fatty acid substrate. Thus, the reactions may produce a product having 3 or 4 or 5 carbon atoms in its chain, respectively with selectivities of at least 50% or at least 60% or at least 70% or at least 80% or at least 90% molar. In other embodiments the predominant product has three fewer carbon atoms compared to the number of carbon atoms in the chain of the hydrocarbon or fatty acid substrate, and in other embodiments the predominant product has four fewer or five fewer carbon atoms in its chain compared to the carbon chain of the hydrocarbon or fatty acid substrate. Additionally, other mono- and di-hydroxy palmitic acid derivatives may be produced. These additional products may be further processed by chemical or other methods into additional desired products as described herein.

The present methods can also produce the dicarboxylic acids products without the hydrocarbon or fatty acid substrate being bound to or by an acyl carrier protein (ACP) at the time of cleavage by the enzyme, or at any point during the reaction.

Without wishing to be bound by any particular theory it is believed that the reaction of the invention proceeds through a step-wise oxidation of the hydrocarbon or fatty acid substrate to Alcohol-A (FIG. 1) followed by the further oxidation and formation of vicinal diols and eventually to the synthesis of a dicarboxylic acid by the further oxidative cleavage of the C—C bond between the diols. A CYP102 enzyme catalyzes these reactions and NADPH can be a cofactor. A carboxylic acid product can also be produced. Thus, the oxidative cleavage may occur through the over-oxidation of the vicinal diols (FIG. 1). In vicinal diols the hydroxyl groups are attached to adjacent atoms.

In some embodiments in addition to the enzymes an oxidizing agent can be included in the reactions. The oxidizing agent can be contacted with the substrate simultaneously with the enzyme or in a separate subsequent step. The oxidizing agents promote the oxidation of adjacent diols or alcohols to the corresponding carboxylic acids with the simultaneous breaking of the C—C bond. Examples of oxidizing agents that can be included in the reactions include, but are not limited to, $H_2O_2/Na_2WO_4$, tungsten-based poly-acids, ruthenium chloride, potassium permanganate or other strong oxidizing agents. In different embodiments the inclusion of one or more oxidizing agents can increase the reaction yield of di-carboxylic acids in any of the methods by at least 30% or at least 50% or at least 70% or at least 100% or at least 150% or from 30%-200% or from 50% to 150% or from 50% to 200% versus in the absence of the oxidizing agent.

Hydrocarbons and Fatty Acids

The hydrocarbons and fatty acid substrates used in the invention can be any hydrocarbon or fatty acid. As used herein the term "hydrocarbon" indicates molecules consisting entirely of carbon and hydrogen atoms, referring to both straight chain hydrocarbons, branched chain hydrocarbons, and cyclic hydrocarbons (e.g., a cycloalkane). A fatty acid molecule as used herein is a carboxylic acid molecule having an aliphatic tail, which can be saturated or unsaturated. They can be (but are not necessarily) derived from triglycerides or phospholipids. They may also be referred to as free fatty acids when not attached to other molecules. The hydrocarbons and fatty acids used in the invention can be either saturated or unsaturated or partially saturated. A hydrocarbon or fatty acid molecule as used herein comprises a hydrocarbon chain within it consisting only of carbon and hydrogen atoms of at least 3 or at least 4 or at least 5 or at least 6 or at least 7 or at least 8 or at least 9 or at least 10 or at least 11 or at least 12 or at least 13 or at least 14 or at least 15 or at least 16 or at least 17 or at least 18 or at least 19 or at least 20 or 22 carbon atoms. In other embodiments the hydrocarbon or fatty acid has 12 or fewer, 13 or fewer, 14 or fewer, 15 or fewer, 16 or fewer, 17 or fewer, 18 or fewer, 19 or fewer, 20 or fewer, 21 or fewer, or 22 or fewer carbon atoms, or up to 22, or up to 24, or up to 26, or up to 28, or up to 30 carbon atoms. The carbon atoms can be part of an aliphatic chain. In other embodiments the hydrocarbon or fatty acid can have from 4 to 20 or from 4 to 22 or from 4 to 24 or from 4 to 26 or from 4 to 28 or from 4 to 30 or from 14 to 20 or from 15 to 22 carbon atoms.

In some embodiments the hydrocarbon or fatty acid substrate molecule can also contain other functional groups in the molecule having atoms other than carbon and oxygen. In other embodiments the substrate does not contain a functional group. The functional groups can include carbon, hydrogen, and oxygen atoms, but in other embodiments can include one or more other atoms such as, for example, nitrogen, phosphorus, and halogens, but in other embodiments can be any atoms. In various embodiments the hydrocarbon chain of the hydrocarbon molecule is as described above and can have a number of hydrogen atoms corresponding to the number of carbons, in a saturated or unsaturated hydrocarbon chain within the hydrocarbon molecule. In some embodiments a hydrocarbon molecule according to the invention has only hydrogen and carbon atoms and, when there is a functional group present, not more than 12% or not more than 13% or not more than 14% or not more than 15% oxygen atoms by number.

In embodiments where the substrate is a fatty acid, it can be a fatty acid between 4 and 28 carbons, or from 15 to 20 carbons, or has 4, 5, 6, 7, 8, 9, 10, 11, 12, 13, 14, 15, 16, 17, 18, 19, or 20 carbon atoms. The carbon atoms can be part of an aliphatic chain, and the aliphatic chain can be a straight or branched aliphatic chain. The fatty acid can be saturated or unsaturated or partially unsaturated. Thus, the fatty acid can have 0, 1, 2, 3, or more than 2 or more than 3 double bonds. In some embodiments the hydrocarbon is a saturated straight chain aliphatic hydrocarbon. Examples of suitable hydrocarbons include, but are not limited to, pentadecanoic acid (pentadecyclic acid, C15), hexadecanoic acid (palmitic acid, C16), heptadecanoic acid (margaric acid, C17), octadecanoic acid (stearic acid, C18), nonadecanoic acid (nonadecylic acid, C19), and eicosanoic acid (arachidic acid, C20). In additional embodiments the hydrocarbon can be propanoic acid (C3), butanoic acid (C4), pentanoic acid (C5), hexanoic acid (C6), heptanoic acid (C7), octanoic acid (C8), nonanoic acid (C9), decanoic acid (C10), undecanoic acid (C11), dodecanoic acid (C12), tridecanoic acid (C13), tetradecanoic acid (C14), heneicosanoic acid (C21), docosanoic acid (C22), tricosanoic acid (C23), tetracosanoic acid (C24), pentacosanoic acid (C25), hexacosanoic acid (C26), heptacosanoic acid (C27), octacosanoic acid (C28), nonacosanoic acid (C29), triacontanoic acid (C30), henatriacontanoic acid (C31), dotriacontanoic acid (C32), tritriacontanoic acid (C33), tetratriacontanoic acid (C34), pentatriacontanoic acid (C35), and hexatriacontanoic acid (C36). Persons of ordinary skill with resort to this disclosure will realize additional hydrocarbon or fatty acid molecules that can be used in the methods of the invention. The invention can also be applied to mixtures of hydrocarbons or fatty acids. A mixture of fatty acids or hydrocarbons useful in the invention can contain more than one type or species of any of the fatty acids or hydrocarbons disclosed herein. In some embodiments the mixture can contain 2 or 3 fatty acids or hydrocarbons disclosed herein. The hydrocarbon or fatty acid can also be any that the enzyme of the invention can over-oxidize and break a C—C bond to produce a dicarboxylic acid product.

Cyclic Hydrocarbons

Cyclic hydrocarbons comprise one or more rings of carbon atoms. The hydrocarbon chain of a cyclic hydrocarbon that consists entirely of carbon and hydrogen atoms can be a part of one or more of the rings. In some embodiments the methods of the invention can be applied to cyclic hydrocarbons or cycloalkanes in the production of dicarboxylic acids. Cycloalkanes are alkane hydrocarbons and have one or more rings of carbon atoms in the chemical structure of the molecule. In some embodiments the methods can be used to convert cyclic hydrocarbons to produce single hydroxylation products (e.g., alcohols, ketones) or diols and keto alcohols. The cyclic hydrocarbons can contain 5 or 6 or 7 or 8 or 9 or 10 or 11 or 12 or 13 or 14 or 15 or 16 or 17 or 18 or 19 or 20 carbon atoms in the ring. In some particular embodiments the cyclic hydrocarbon can be the cycloalkanes cyclooctane or cyclodecane, or any cyclic hydrocarbon.

Figure 2:
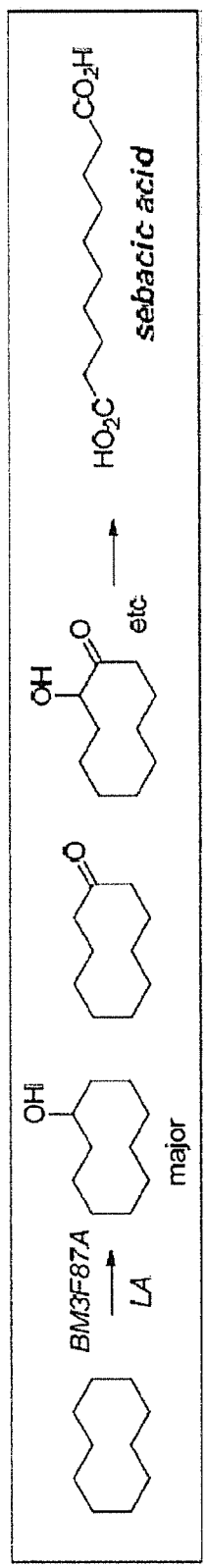
FIG. 2 is a pathway showing the oxidation of a cyclic hydrocarbon (cyclodecane) to produce a dicarboxylic acid product.

In one embodiment cyclodecane is oxidized in the methods to produce a heptanedioic acid (sebacic acid) dicarboxylic acid product, as shown in FIG. 2 and further discussed in Example 3. The enzyme utilized in this embodiment was the CYP102 enzyme BM3-F87A. Other cyclic hydrocarbons can also be utilized in the present invention to form corresponding dicarboxylic acids.

Dicarboxylic Acids

The methods of the invention produce dicarboxylic acid products. The reactions of the invention are able to produce dicarboxylic acids having an even or odd number of carbon atoms in the carbon chain, thus the product can be a dicarboxylic acid having 4 or 5 or 6 or 7 or 8 or 9 or 10 or 11 or 12 or 13 or 14 or 15 or 16 or 17 or 18 or 19 or 20 or 21 or 22 or more than 22 carbon atoms. For example the methods of the invention can be applied to palmitic acid (C16) to produce tridecanedioic acid (C13). In another example the methods can be used to convert stearic acid (C18) to pentadecanedioic acid (C15). The methods can also produce a mixture of dicarboxylic acid products, which may be present in varying portions. The dicarboxylic acid product can also be a mono-unsaturated or di-unsaturated or poly-unsaturated dicarboxylic acid.

Persons of ordinary skill with resort to this disclosure will realize that the enzymes used in the methods can be engineered to act on specific substrates and produce specific products. It is possible to also design processes that utilize both chemical and enzymatic methods to produce specific products of interest from specific substrates. By using a combination of chemical and enzymatic methods it is possible to design processes for transforming all or substantially all carbon in the starting substrate or reactant molecules into a desired product. The desired product can be any described herein. For example, with reference to FIG. 1 residual Diol-A that may be present after incomplete oxidation of substrates can be processed to a desired product using one or more additional chemical steps. In the same manner other reactants produced from incomplete reactions or as side products can also be processed to desired products by one or more additional chemical or enzymatic steps. An isolation or purification step can also be added if desirable, which involves the isolation or purification of a desired product from a reaction product mixture. In such manner, by combining chemical and enzymatic steps, product yields can be increased. By substantially all carbon is meant at least 90% of carbon atoms.

In another embodiment the products are not dicarboxylic acids but are precursors to dicarboxylic acids, for example, diols or keto alcohols that can be converted into dicarboxylic acids with one or more additional steps. The precursors may be useful chemicals, or they may be further processed into dicarboxylic acid products, as desired.

Di-carboxylic acids can be purified from reaction media by various methods. Di-carboxylic acids have limited solubility in acidic aqueous media. Therefore, methods can be employed involving one or more steps of the precipitation of di-carboxylic acids by lowering the pH of the reaction solution. They can also be extracted from the reaction mixture at acidic pH (e.g., 1-4) in one or more steps using various organic solvents such as ethers (diethyl, dibutyl, methyl-tert-butyl ether, etc.), esters (ethyl acetate, propyl acetate, butyl acetate, etc.) or other solvents such as, for example, petroleum ether, hexane, toluene etc., or any combination of them.

Additional examples of purification methods that can be employed include one or more steps of precipitation by the addition of aqueous, miscible, organic solvents (e.g., ethanol). Insoluble salts can also be produced, for example by the addition of Ca(OH)2. Another method that can be employed is the esterification of the di-carboxylic acids to form their corresponding diesters using MeOH, EtOH, PrOH, BuOH, iBuOH or other alcohols. Esters can be formed in situ in the aqueous reaction media using enzymes (such as esterases), or by incubating the di-carboxylic acids in these alcohols after they have been precipitated as described above. Esterification of precipitated di-carboxylic acids can be catalyzed by an enzyme (e.g., esterase, lipase) or by a chemical catalyst (e.g., BF3, acid, base etc). Esters can then be distilled under reduced pressure or can be purified by chromatography. Any of the methods described herein can include one or more of the above-described steps to purify or isolate the di-carboxylic acid product.

Enzymes

The enzymes utilized in the methods can be bacterial enzymes, which in some embodiments can be a fatty acid hydroxylase flavocytochrome P450 enzyme. In one embodiment the enzyme is a microbial cytochrome P450 enzyme, which can be a bacterial enzyme. In other embodiments plant, animal, mammal, insect, or fungal cytochrome P450 enzymes can be used. A bacterial cytochrome P450 enzyme can contain a ferredoxin reductase and a ferredoxin, which can be present as a single peptide or as separate proteins, and which transfer electrons to P450. In one embodiment the enzyme is a member of the P450 enzyme sub-family CYP102. It was discovered unexpectedly that the members of this class of enzymes have the ability to over-oxidize hydrocarbon and fatty acid substrates and break a C—C bond in the substrate. Enzymes of this sub-family contain both the heme domain, which performs the oxidation of the substrate, and the reductase domain, which reduces the heme iron in each catalytic cycle. With these domains present in a single protein increased activity and increased catalytic turnovers are available. The P450 heme domain of the enzyme can over-oxidize saturated hydrocarbons, fatty acids, diols, or keto alcohols to produce the dicarboxylic acid with the concomitant breaking of the C—C bond. The enzymes of the invention are able to do this even to free fatty acids, meaning fatty acids that are not bound to ACP. Portions of the enzymes that also have these abilities are referred to as functionally active fragments of the enzymes, and they can also be used in the methods. In various embodiments functionally active fragments can have at least 50% or at least 70% or at least 90% of the described function of the full molecule, and can be of any portion or sub-portion of the sequence of the full molecule having the stated % function compared to the full molecule.

The enzyme(s) can be derived from a bacterium, e.g., a bacterium of the genus *Bacillus*, or can be derived or synthesized and expressed in *E. coli* or another appropriate host cell. In one embodiment the particular species of *Bacillus* is *Bacillus megaterium*. The enzyme can be BM3, otherwise known as CYP102A1 (EC1.14.14.1), which is a fatty acid hydroxylase from *Bacillus megaterium*. BM3 contains a P450 heme domain fused to the eukaryotic-like diflavin reductase partner (cytochrome P450 reductase) in a single polypeptide chain, and therefore is catalytically self-sufficient as a monooxygenase. The enzyme can also be a homolog of BM3 having a stated percent sequence identity to BM3. BM3 and other members of the CYP102 sub-family catalyze the NADPH-dependent hydroxylation of long-chain fatty acids at the $\omega$-1, $\omega$-2, and/or $\omega$-3 positions. But in various embodiments many enzymes and homologs of enzymes described herein have the recited characteristics and are useful in the methods of the invention. In other embodiments the enzyme can also be YetO (CYP102A2) (EC1.14.14.1) from a *Bacillus* or a homolog thereof, or can be yrhJ (CYP102A3) (EC1.14.14.1) or a homolog thereof or any enzyme in the CYP102 sub-family or a homolog thereof. YrhJ can be derived from *Bacillus amyloliquifaciens* (strain FZB42, among other strains) and has a length of 1053 amino acids. CYP102A2 and CYP102A3 can be derived from *Bacillus subtilis* and are both homologs of BM3, and are both natural water-soluble fusion proteins. The enzymes used in the methods of the invention can be soluble enzymes, which means in their natural state the enzymes (or the enzyme from which a homolog is derived) are present in the cytosol of the cells from which they are derived. Enzymes that exist primarily in the cell membrane in their natural state (and homologs thereof) are not considered soluble enzymes. Other enzymes finding use in the present invention include Cyp96A and others.

In various embodiments the enzyme used in the invention can be a cytochrome P450 enzyme of the sub-family CYP102, or a homolog thereof. BM3 can be derived from *B. megaterium* and techniques are available for producing suitable homologs, for example site-directed mutagenesis. In one embodiment the enzyme is YetO, the nucleic acid and protein sequences of which are disclosed in the accompanying sequence listings as SEQ ID NO: 3 (nucleic acid) and SEQ ID NO: 4 (protein). This enzyme can be isolated and cloned from gDNA, or can be synthesized and optimized for recombinant expression in an appropriate host organism such as, for example, *E. coli, Pseudomonas,* or *Bacillus*. Many site-specific mutants can be derived. FIG. 3 illustrates various homologs that have been derived from BM3, and the exemplary sequences of some homologs are disclosed in the accompanying sequence listings as Bac0018 (SEQ ID NO: 5) and Bac2875 (SEQ ID NO: 7), as well as some wild type sequences BM3-wt (SEQ ID NO: 1—DNA and SEQ ID NO: 2—amino acid) and corresponding protein sequences. But persons of ordinary skill with resort to this disclosure will be able to derive a large number of suitable homologs, to BM3 or to other P450 enzymes.

Homologs of any of the enzymes disclosed herein can also be used as the enzyme in the methods. In various embodiments the enzyme utilized in the method can have at least 50% sequence identity to the cytochrome P450 enzyme BM3-wt (CYP102A) from *Bacillus megaterium* or YetO from *Bacillus subtilis* (CYP102A2) or yrhJ-wt. In various other embodiments the enzyme of the methods can have at least 55% or at least 60% or at least 70% or at least 80% or at least 90% or at least 95% or at least 98% or at least 99% sequence identity to BM3-wt or YetO-wt or yrhJ-wt. In other embodiments the invention provides an enzyme having 50-99% sequence identity to CYP102A or YetO wild type enzymes or 50-90% or 55-90% or 60-90% or 80-90% or 55-99% or 60-99% or 70-99% or 80-99% or 90-99% or 95-99% or 98-99% sequence identity to CYP102A or YetO wild type enzymes. A number of different search algorithms have been developed, including but not limited to the suite of programs referred to as BLAST programs. There are two implementations of BLAST designed for protein sequence queries (BLASTP and TBLASTN) (Coulson, Trends in Biotechnology: 76-80, 1994; Birren et al., Genome Analysis, I: 543, 1997). Such methods involve alignment and comparison of sequences. The BLAST algorithm calculates percent sequence identity and performs a statistical analysis of the similarity between the two sequences. The software for performing BLAST analysis is publicly available through the National Centre for Biotechnology Information. Other such software or algorithms are GAP, BESTFIT, FASTA and TFASTA. GAP uses the algorithm of Needleman and Wunsch (J. Mol. Biol. 48: 443-453, 1970) to find the alignment of two complete sequences that maximizes the number of matches and minimizes the number of gaps. In the invention, one or more of these methods can be used to calculate the percent amino acid or nucleotide sequence identity between two homolog molecules.

The methods and/or reactions described herein can be performed in vitro or in vivo in a suitable host cell. In some embodiments any one or more of the nucleic acid or protein/peptide sequences disclosed herein can be comprised in a vector. In some embodiments the vector can contain one or more selection markers. Host cells can be transformed with the vector and the methods and reactions described herein carried out in the organism. The organisms transformed can be an appropriate yeast or bacterial species. Examples include, but are not limited to, bacteria in the Enterobacteriaciae family, such as *E. coli, Yersinia, Klebsiella, Shigella, Hafnia* (e.g., *alvei*). When a yeast is used, any suitable yeast can be used (e.g., *Saccharomyces, Candida*, etc). In one embodiment the invention provides a recombinant organism or cell comprising an exogenous nucleic acid described herein (e.g., any one or more of SEQ IDs 1 or 2 or 3 or 4 or 5 or 6 or 7. "Exogenous nucleic acid" refers to a nucleic acid not found in the organism in its natural environment.

The enzymes utilized in the methods of the invention can have selectivity for a $\omega$-2 or $\omega$-3 fatty acid diol. In various embodiments the enzyme has a selectivity for either an $\omega$-2 or $\omega$-3 fatty acid diol of at least 50% or at least 60% or at least 70% or at least 80% or at least 90% molar selectivity, meaning that the enzyme will cleave the stated percentage of times the $\omega$-2 or $\omega$-3 fatty acid diol.

The invention also provides a composition containing any of the enzymes or stated homologs thereof described herein. In various embodiments the enzymes can be provided in a dried form in a container, or in a liquid form in a container. The enzyme compositions can also be a purified enzyme composition, for example being at least 90% purified w/w or at least 95% pure w/w or at least 98% pure w/w or at least 99% pure w/w. Any of these purified enzyme compositions or any combination thereof can be used in the methods of the invention.

The invention can also provide a kit for conducting methods of the invention. The kits can contain any one or more compositions of the invention provided in a container (either individually or together) and, optionally, instructions for using the composition to conduct a method of the invention and/or a link to a website providing such instructions and/or information about the methods and/or about conducting the methods. The kit can also contain buffers for conducting the methods.

Cell or Cell-Free Systems

The methods, compositions and reactions of the invention can be performed or applied in either a cell culture system or a cell-free system. When cell culture is used it can be either a bacterial cell culture (e.g., using bacteria described herein or other appropriate species) or a yeast cell culture or an insect cell culture. In some embodiments the methods can be applied in a whole cell system utilizing cells that over-express a CYP102 enzyme, which in some embodiments is expressed in the cell as an exogenous enzyme. Any suitable enzyme of the CYP102 sub-family or a homolog thereof can find use in the present invention. In performing the methods cells can be mixed with any appropriate hydrocarbon or fatty acid substrate (or mixture of such substrates) as described herein. Additionally, one or more sugar molecules (e.g., glucose, glycerol, formic acid) can also be present in the mixture for the generation of reducing equivalents. In some embodiments recombinant proteins producing enzymes or other components of the system can be expressed on plasmids or other extra-chromosomal DNA. In one embodiment the enzyme that breaks a C—C bond of a hydrocarbon or fatty acid substrate is expressed on a plasmid comprised in bacteria in a bacterial fermentation.

The methods, compositions and reactions of the invention can also be performed or applied in a cell-free system. The methods can be performed or applied in a crude lysate, or in other embodiments purified enzyme (or a combination of enzymes) can be used in a free soluble enzyme or immobilized on a solid support. A crude lysate is the solution produced when cells are destroyed by lysing or disrupting their cell membranes, and in one embodiment at least 50% of the cells in a medium or solution are lysed or destroyed to produce the crude lysate, but in other embodiments at least 75% or at least 90% or at least 95% or at least 99% f the cells in the medium or solution are destroyed or lysed to produce the crude lysate. Catalytic amounts of NAD and/or NADP and/or another desirable co-factor, as well as a desirable co-factor recycling system can also be present in the reaction mixture, for example a glucose/glucose dehydrogenase or formate/formate dehydrogenase system, or another appropriate system for recycling co-factors. In some embodiments the methods of the invention are performed in a test tube, centrifuge tube, multi-well plate, 96 cell plate, fermenter, flask, cuvettes, glass or plastic vessel, or other vessel that contains the reactants. The methods can involve isolating or obtaining enzyme from a microorganism grown on a nutrient agar or nutrient plate or in a nutrient medium. The methods can also be performed using live or immobilized cells containing or expressing the enzymes.

Any of the methods described herein may involve one or more steps of culturing cells or host cells (either of which examples are provided herein), and/or one or more steps of lysing, disrupting, or destroying the cells or host cells before contacting the hydrocarbon or fatty acid substrate with one or more of the enzymes described herein. The method can also involve one or more steps of producing a dicarboxylic acid product and/or performing a purification step for one or more dicarboxylic acid products from a cell culture or lysate.

Example 1—Enzyme Engineering

This example shows the engineering of wild-type (wt) BM3 and wild-type (wt) YetO to produce a group of mutant enzymes having the desirable activities of sub-terminal over-oxidation of fatty acids and the breaking of the C—C bond. BM3 (or CYP102A1) from *B. megaterium* and one proprietary homolog from a *Bacillus* strain (YetO from *Bacillus* 15_F03) were cloned. Medium homology is shared between BM3 and YetO (60% identity, 75% similarity). The natural gene sequences were used in all plasmids. The YetO gene was PCR-cloned from gDNA, while a synthetic gene using the natural DNA sequence was made for BM3. Various site specific mutants from these sequences were then created as shown in Table 1.

TABLE 1

Initial BM3 and homologs cloned

| Enzyme (Source) | Source | Mutation | pSGI | Vector |
| --- | --- | --- | --- | --- |
| BM3 (P14779) | *B. megaterium* | — | 118 | pET24 |
| BM3 (P14779) | *B. megaterium* | F87A | 004 | pET24 |
| BM3 (P14779) | *B. megaterium* | F87A (w/HisTag) | 014 | pET28 |
| yetO | *Bacillus* 15_F03 | — | 040 | pET24 |
| yetO | *Bacillus* 15_F03 | F89A | 055 | pET24 |

TABLE 1-continued

Initial BM3 and homologs cloned

| Enzyme (Source) | Source | Mutation | pSGI | Vector |
|---|---|---|---|---|
| yetO | Bacillus 15_F03 | F89I | 056 | pET24 |
| yetO | Bacillus 15_F03 | F89S | 057 | pET24 |
| yetO | Bacillus 15_F03 | F89V | 058 | pET24 |

Figure 4B:
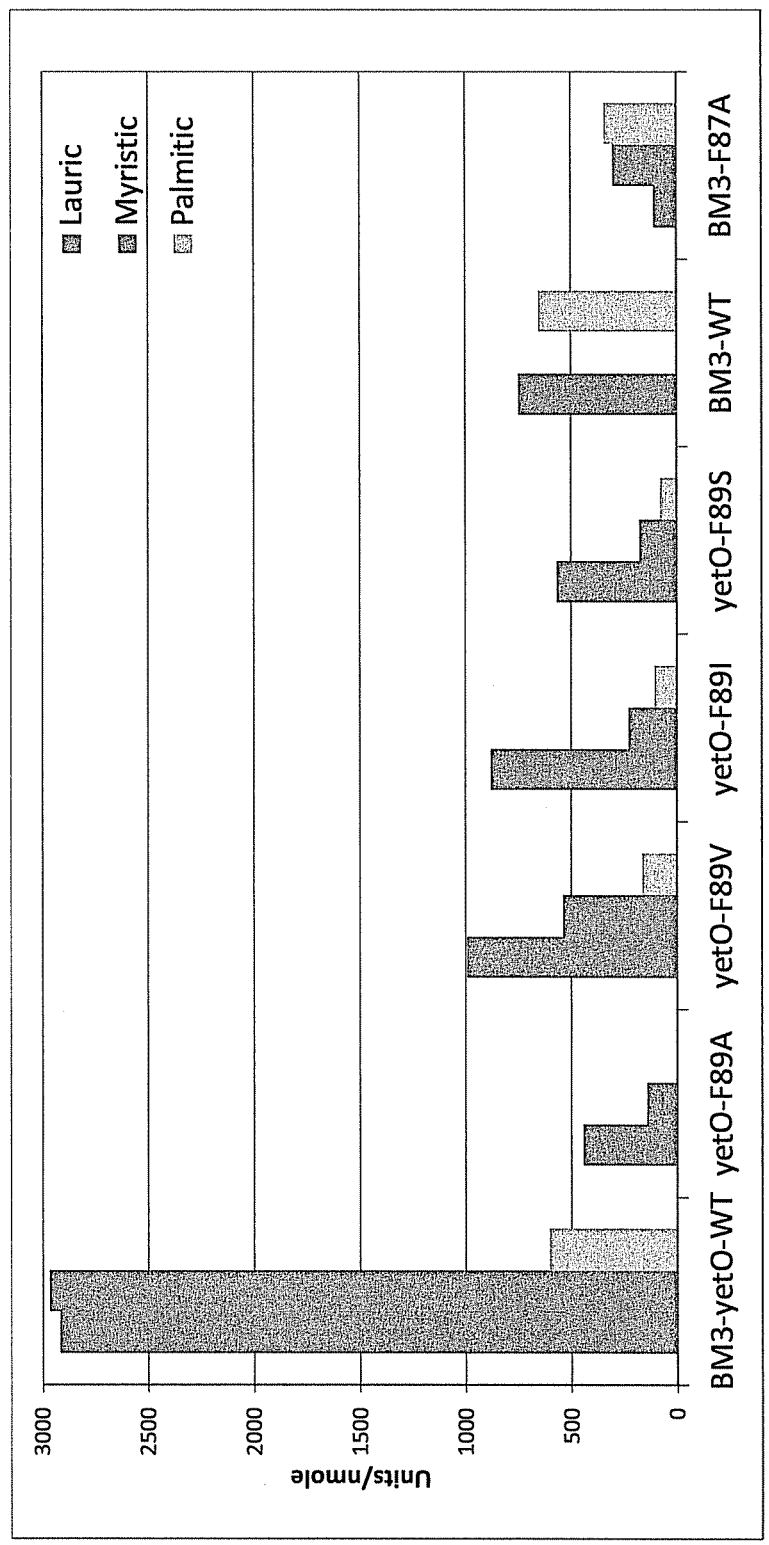
FIG. 4b is a bar chart showing activity comparisons of BM3, YetO, and selected mutant enzymes; bars are, left to right, lauric, myristic, and palmitic.

The sequences are shown herein. For F87 (in BM3) and F89 (in YetO), this phenylalanine was site mutated to alanine in BM3, and to either alanine, isoleucine, serine, or valine to produce the mutants as indicated in Table 1. Two more BM3 homologs were cloned from two Bacillus strains. The native genes of these enzymes were amplified by PCR from genomic DNA and were cloned into pET24a vector. Good functional expression in E. coli was obtained for both enzymes as indicated by their peaks at 450 nm using standard CO binding assays. Their pairwise percent identities with BM3-wt and YetO-wt are listed in FIG. 3b, which shows that the wild-type BM3 does not necessarily possess a very high degree of homology to the two BM3 mutants. Substantial variation is possible while retaining enzymatic activity, is illustrated in FIG. 4. The two functionally expressed enzymes were characterized for both NADPH depletion and overnight reactions on fatty acids. For NADPH depletion assays, 40 µL of lysate was added to 160 µl reaction buffer (4 mM fatty acid, 0.25 mg/mL NADPH) in 96-well microtiter plates. These reaction conditions resulted in lower specific rates than seen in cuvettes but enzymes showed the same relative specific rates when compared to each other. The two modified enzymes showed specific rates between those of the BM3s and YetOs with preference for palmitic and myristic acids, as seen in FIG. 4b.

FIG. 4a shows the hydroxylation activities of BM3, YetO and selected mutants with various fatty acids and FIG. 4b shows the activity comparison of BM3, YetO, and various enzyme mutants. YetO-wt gives similar oxidation products (hydroxylation at ω-1, 2, 3) as BM3-wt when reacted with lauric acid, but there are differences in the reactivity between these two enzymes. The activity data of FIG. 4b shows that YetO-wt has a preference for lauric (C12) and myristic (C14) compared to palmitic (C16) acid. In contrast, BM3-wt possesses similar activity for lauric and palmitic acids, but its activity is significantly lower for lauric acid compared to YetO-wt. Furthermore, BM3-F87A shows a reversal of fatty acid preference (palmitic being the highest amongst C12/C14/C16) compared to the equivalent mutant(s) of YetO.

Figure 5:
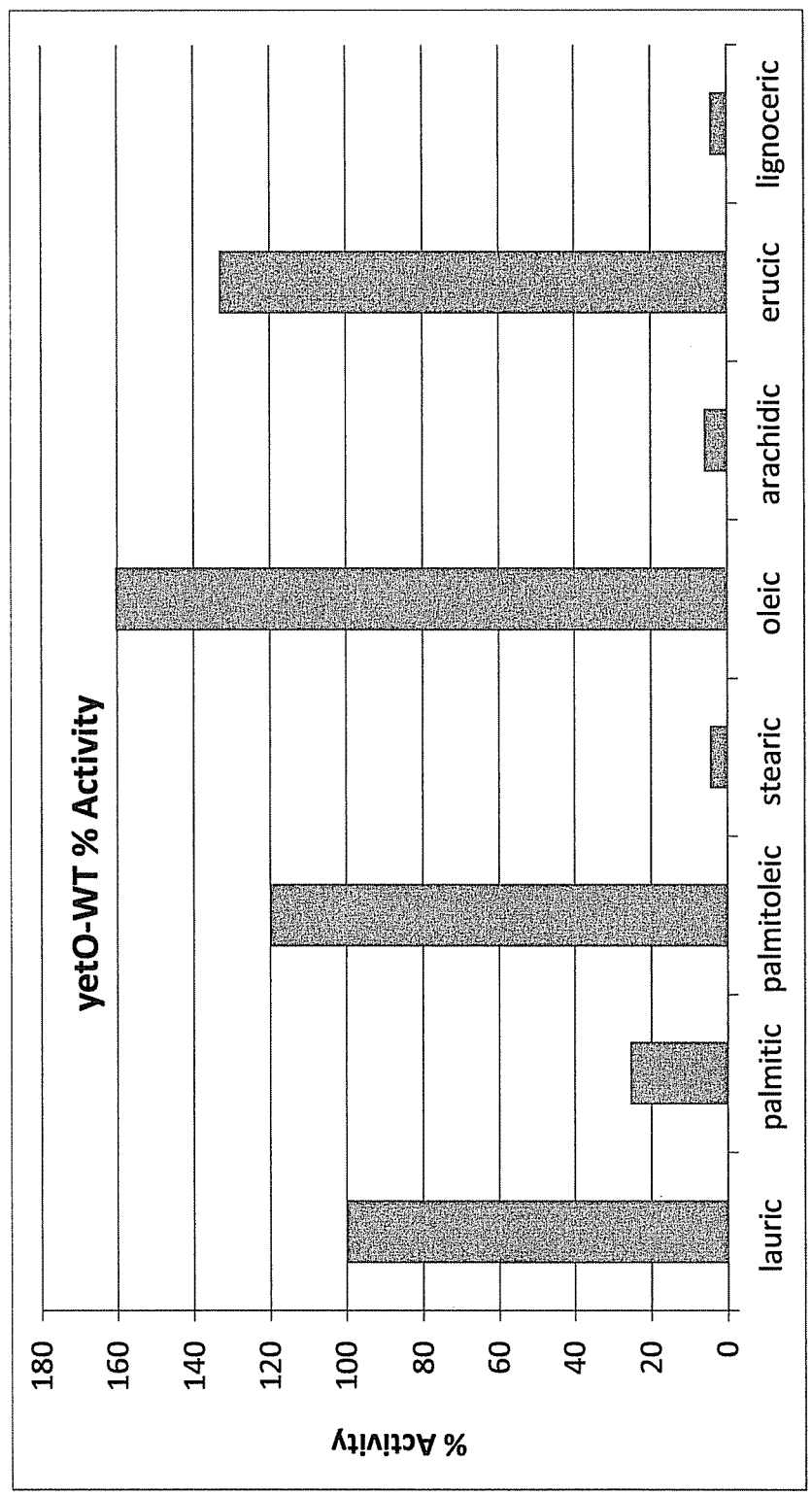
FIG. 5 provides a bar graph of the relative activities of YetO with different saturated and unsaturated fatty acids compared to lauric acid. Activities in FIG. 5 were calculated by measuring NADPH depletion in cuvette assays using the fatty acids as substrates.

Introducing unsaturation to the fatty acid increased the activity of YetO-wt even to fatty acids longer than palmitic, or to fatty acids whose saturated analog was very low or not active at all (FIG. 5). This is shown in the reactivity comparisons between palmitic and palmitoleic, stearic and oleic and even arachidic and erucic. Note that similar reactivities have been reported with BM3-wt.

For quantitative analysis of products from reactions of the enzymes on fatty acids, cell-free reactions with crude lysate were performed. Crude lysate containing each P450 enzyme was mixed with a reaction mixture (100 mM potassium phosphate pH 7.8; 1-5 mL total volume; 8/2, v/v, reaction mix/P450 lysate) containing 2-5 mM fatty acid, 1.0 mM NADPH, 30 mM glucose, and 1 mg/mL glucose dehydrogenase. The glucose/GDH-105 system regenerates NADPH from NADP by the concomitant oxidation of glucose to gluconate. After overnight incubation at 30° C. with good shaking, crude reaction mixtures were mixed with 1-5 drops trifluoroacetic acid (TFA) and equal volume tetrahydrofuran (THF). After centrifugation to precipitate the insoluble protein, samples were analyzed by HPLC-MS.

Figure 6A:
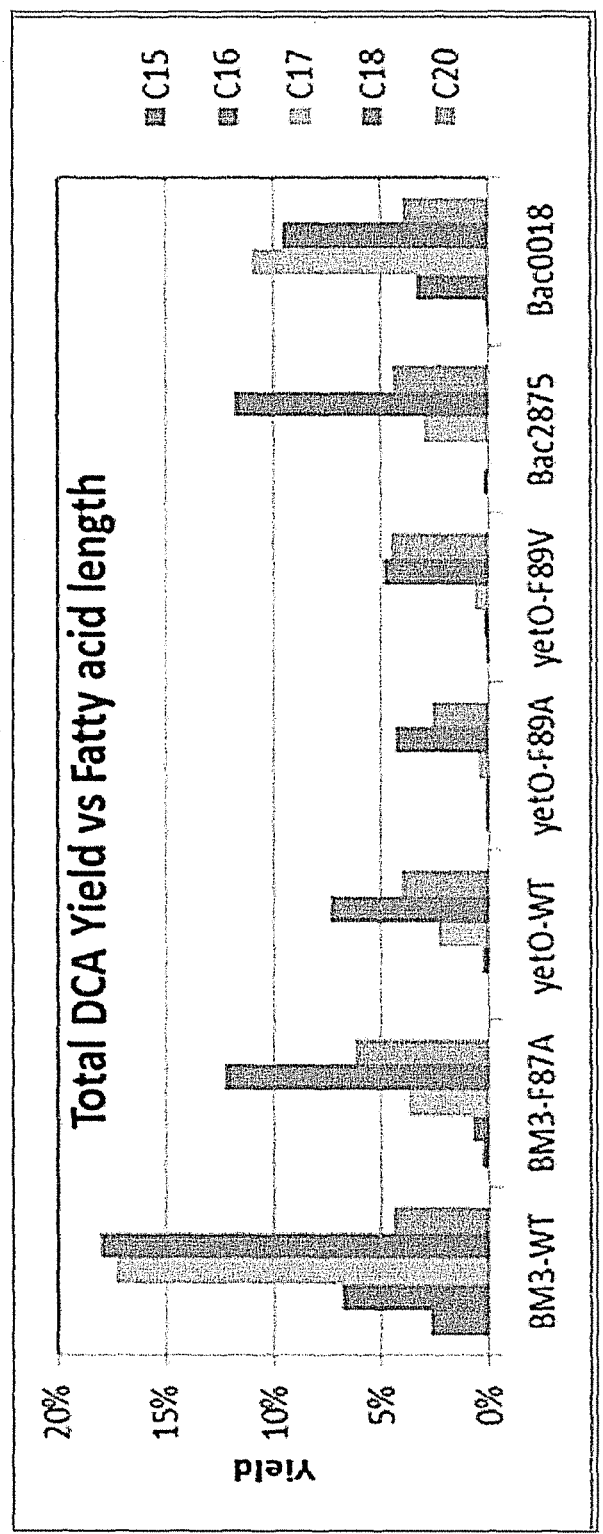
FIG. 6a provides a bar graph of the total yields of dicarboxylic acids (DCAs) vs. fatty acid length.
Figure 6B:
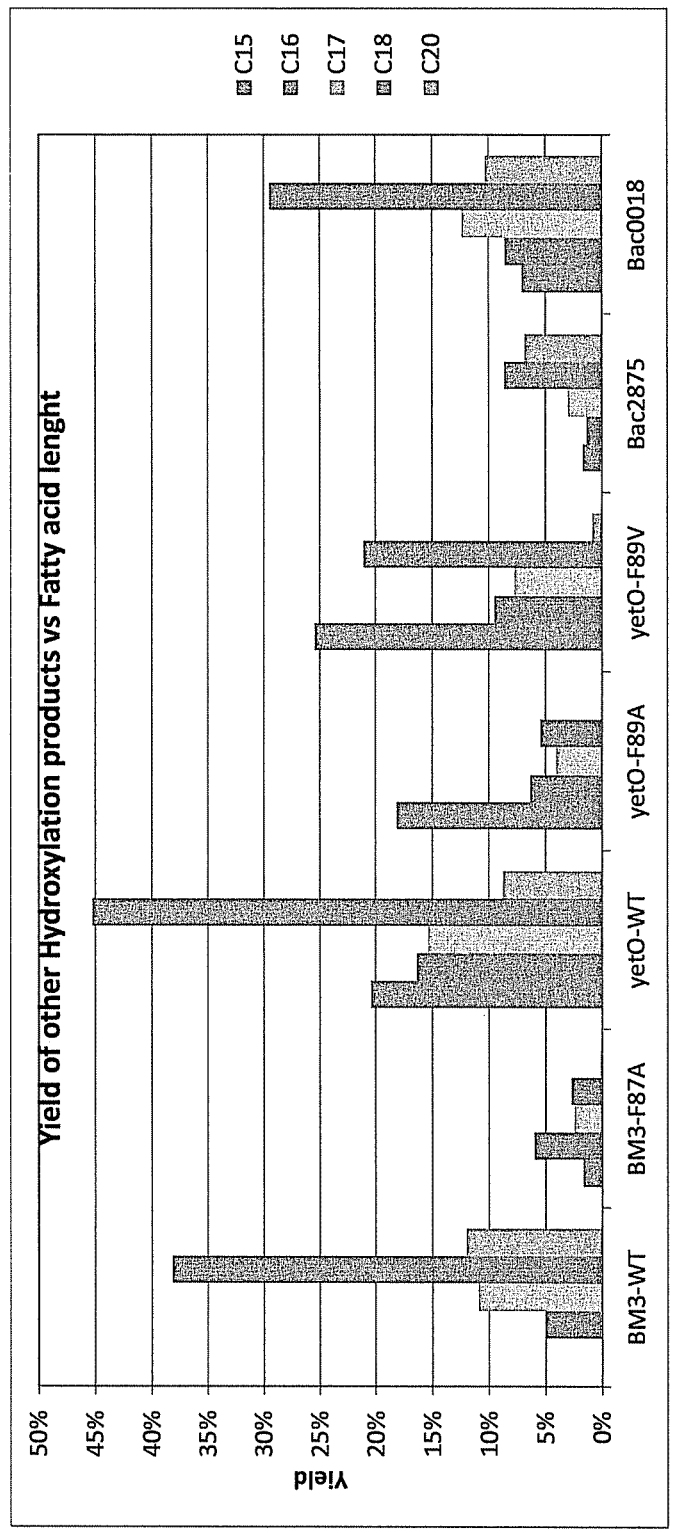
FIG. 6b provides a bar graph of the yields of other hydroxylation products vs. fatty acid length. Bars are, left to right, C15-C20.

Reactions were run on lauric (C12), pentadecanoic (C15), palmitic (C16), heptadecanoic (C17), stearic (C18), arachidic (C20), and lignoceric (C24) acids. The reactions on lauric acid produced a mixture of products formed from hydroxylation at the ω-1, ω-2, and ω-3 positions, without any dicarboxylic acids. Reactions on fatty acids with lengths C15-C20 produced several hydroxylation products and dicarboxylic acids (DCAs) resulting from internal C—C bond cleavage. The concentrations of these products were estimated using calibration curves for the available products (single hydroxylation products, dicarboxylic acids, etc.). FIG. 6a shows total yields of all DCAs and hydroxylation products likely in the pathway to DCA formation. BM3-WT and Bac0018 produce the most DCAs, but the YetO enzymes all produce more hydroxylation products than the other enzymes. The concentration of hydroxylation products in these reactions is also higher than the concentration of DCAs in the best reactions. The enzymes produce large amounts of DCAs from C17 fatty acid, but the yields for the C18 fatty acid are actually higher since the solubility of this substrate is lower and thus there was less starting material present. The YetO enzymes produced small amounts of DCAs but high amounts of other hydroxylation products, as shown in FIG. 6b. These enzymes had lower P450 concentrations in the crude lysate (1-2 µM vs. 4-10 µM) and thus DCA yields may be higher if their concentrations were increased.

Figure 7:
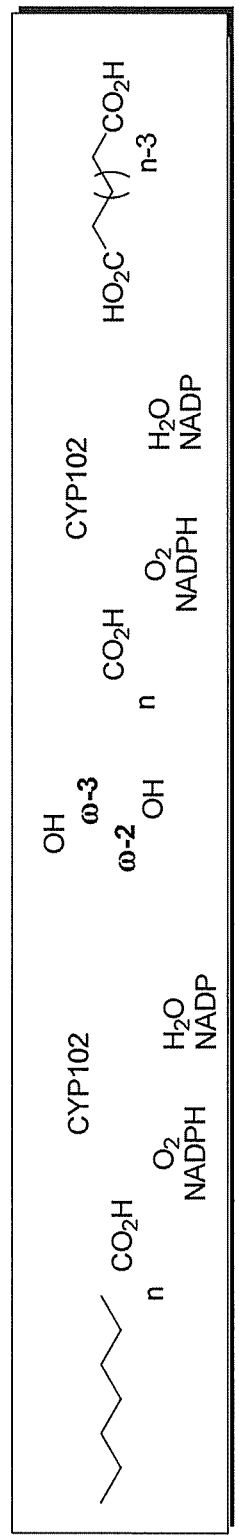
FIG. 7 provides a schematic diagram of the oxidation of C15-C20 fatty acids by CYP102 enzymes.
Figure 8A:
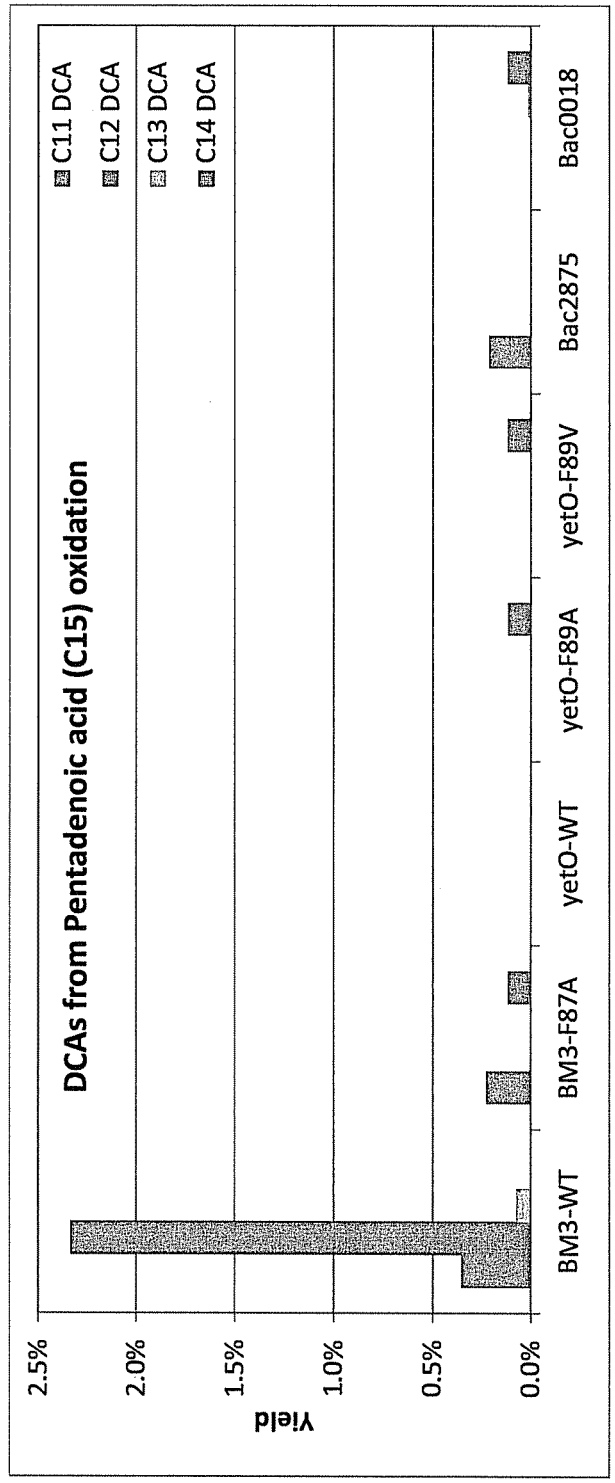
FIGS. 8a-8c provide bar graphs illustrating DCA profiles of CYP102 enzymes with C15-C17 fatty acids. Bars are, left to right, (C15) C11-C14; (C16), C12-C14; (C17), C13-C15.
Figure 8B:
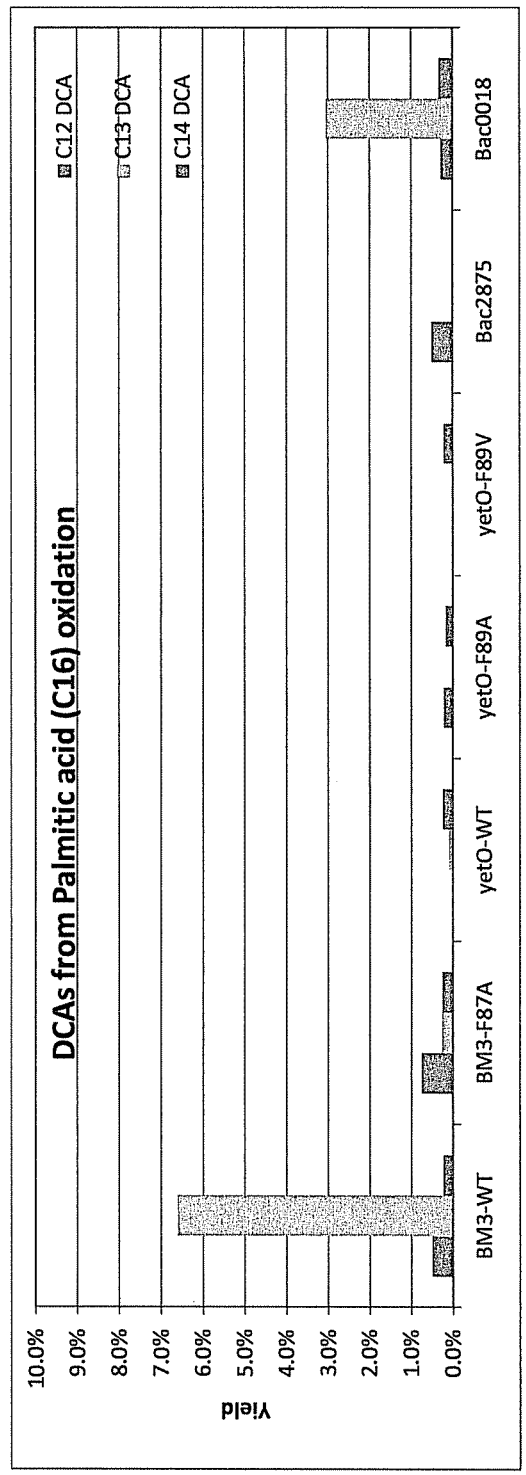
Figure 8C:
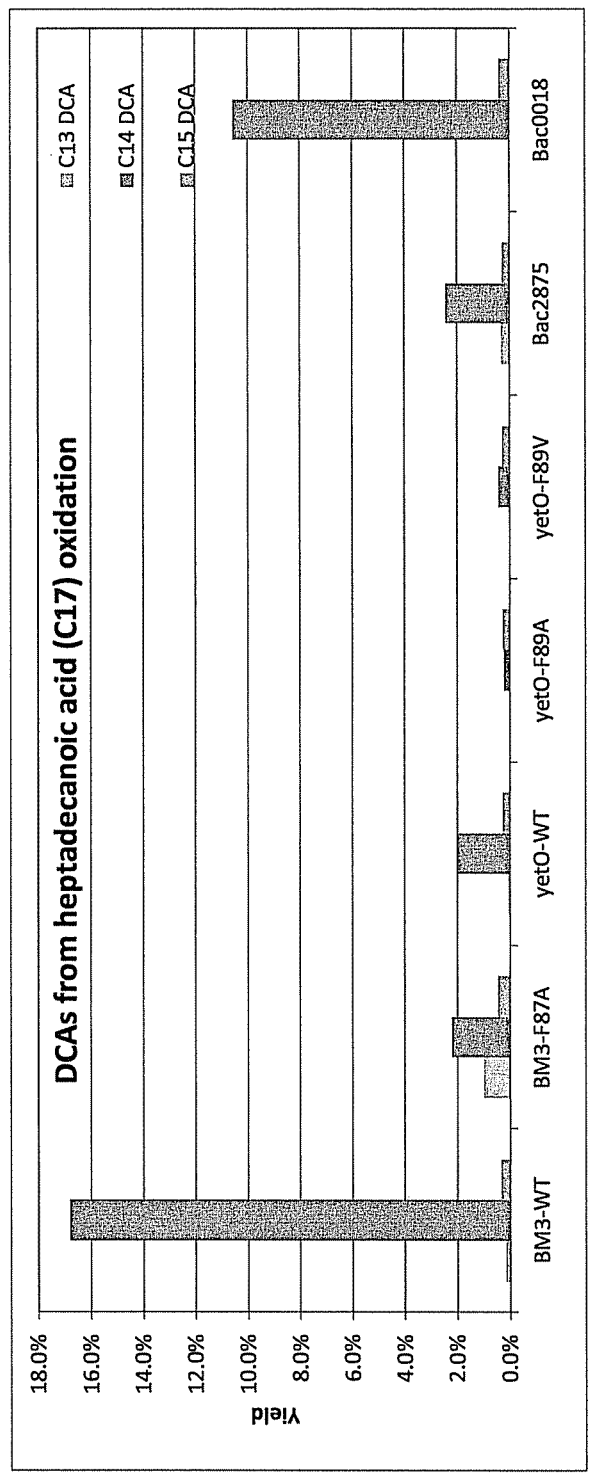
Figure 9A:
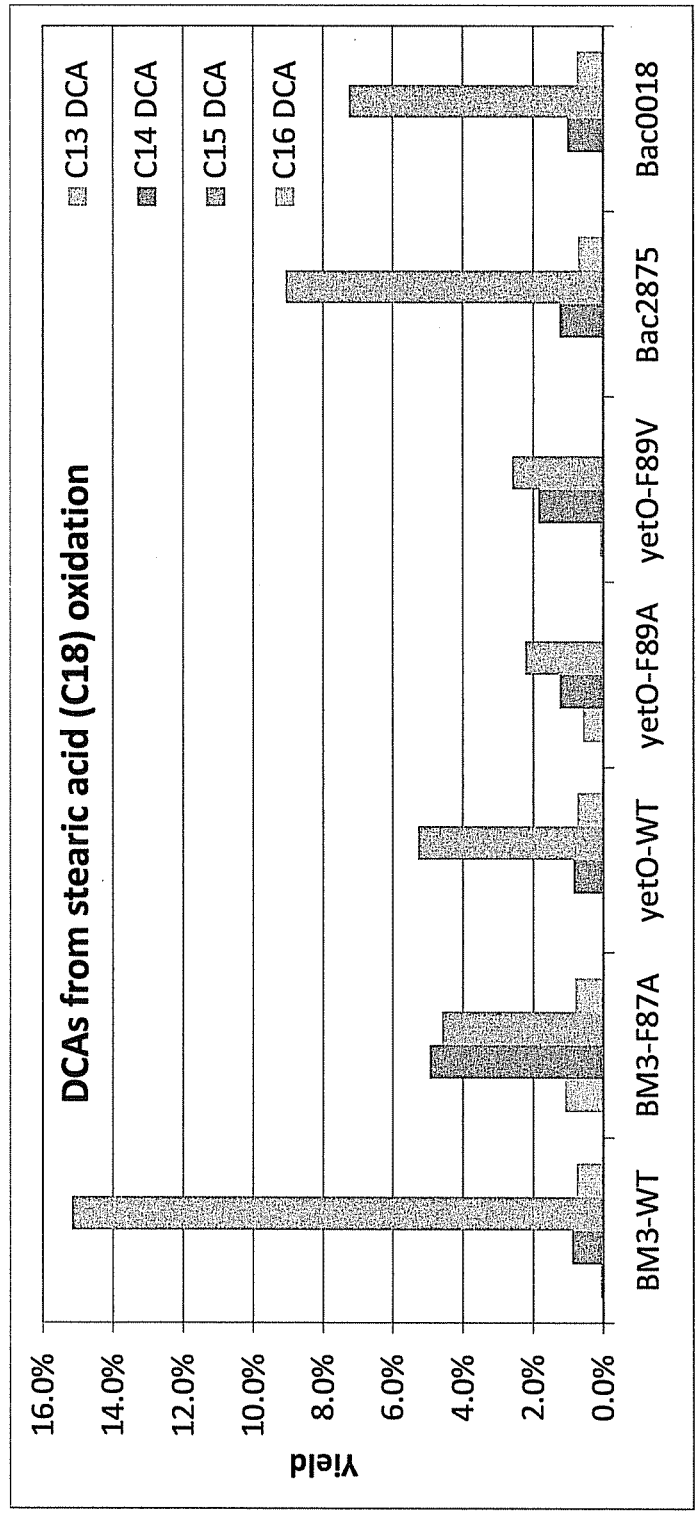
FIGS. 9a-9b provides bar graphs illustrating DCA profiles of CYP102 enzymes with C18 and C20 fatty acids. Bars are, left to right, (C18), C13-C16; (C20), C13-C18.
Figure 9B:
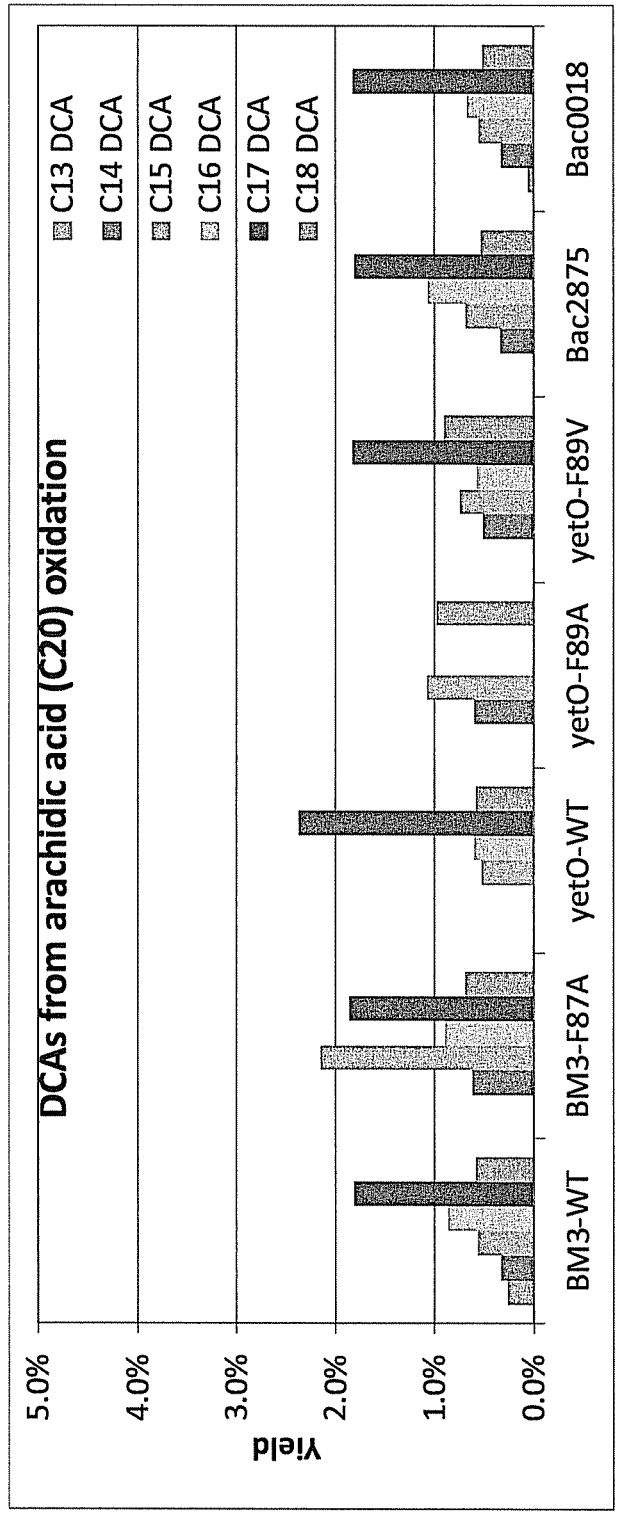

Both BM3 and the three CYP102 enzyme homologs cloned here perform sub-terminal hydroxylation at the ω-1, ω-2 and ω-3 carbons with lauric acid. The oxidation of longer fatty acids (C15-C20) produces alcohols and diols with the same preferences, and their over oxidation is the source of the observed dicarboxylic acids with three less carbons, as illustrated in FIG. 7. It is believed that the diols and keto alcohols that accumulate during the oxidation of C15 to C20 fatty acids with the CYP102 tested herein are vicinal with ω-2 & 3 selectivity. For a fatty acid of length N, DCAs of length N-7 to N-2 were detected, as illustrated in FIGS. 8-9.

Example 2—Oxidation of Palmitic Acid with BM3-YetO

Strain BL21DE3/pSGI-040 (pET24a-BM3-yetO-WT) was grown on 150 mL of M9TV/TB (3/1 v/v)+glucose (2 g/L)+FeCl3 (0.05 mM) in a baffled flask (500 mL). Cells grew at 30° C. for 3-4 h until OD600~0.5 was reached. At this point 0.5 mM δ-aminolevulinic acid and 0.25 mM IPTG were added and the flask was moved into a shaker at RT (~23° C.) where it was allowed to shake for an additional 16 h at 120 rpm.

Cells were harvested by centrifugation and were frozen at −80° C. for at least 1 h. Frozen cells were re-suspended in 15 mL of lysis buffer (100 mM potassium phosphate, 10% glycerol (v/v), 1 mM DTT and 1 mg/mL lysozyme). After thawing the pellet it was incubated on ice for 15 min before cells were sonicated twice. Lysed cells were centrifuged at 12,000 rpm to precipitate insoluble cell debris. Clarified lysate was used without any further purification in enzymatic reactions. Approximately 8-10 uM (or nmole/mL) of P450 was calculated in the lysate.

Enzymatic reactions were prepared by mixing 0.25 mL of the above enzyme lysate with 0.75 mL of reaction buffer. The reaction buffer contained 100 mM potassium phosphate pH=7.8, 50 mM glucose, 1 mM NADP, 1.5 mg/mL glucose dehydrogenase and 2.5 mM lauric acid. The reaction was moved in a 10 mL borosilicate test tube and was thoroughly shaken at 30° C. for 12 h. Sample preparation: in the 1 mL of the reaction add 50 uL of HCl (3M) and 1 mL MeOH. The sample was centrifuged to precipitate proteins and submit for HPLC analysis.

Figure 10:
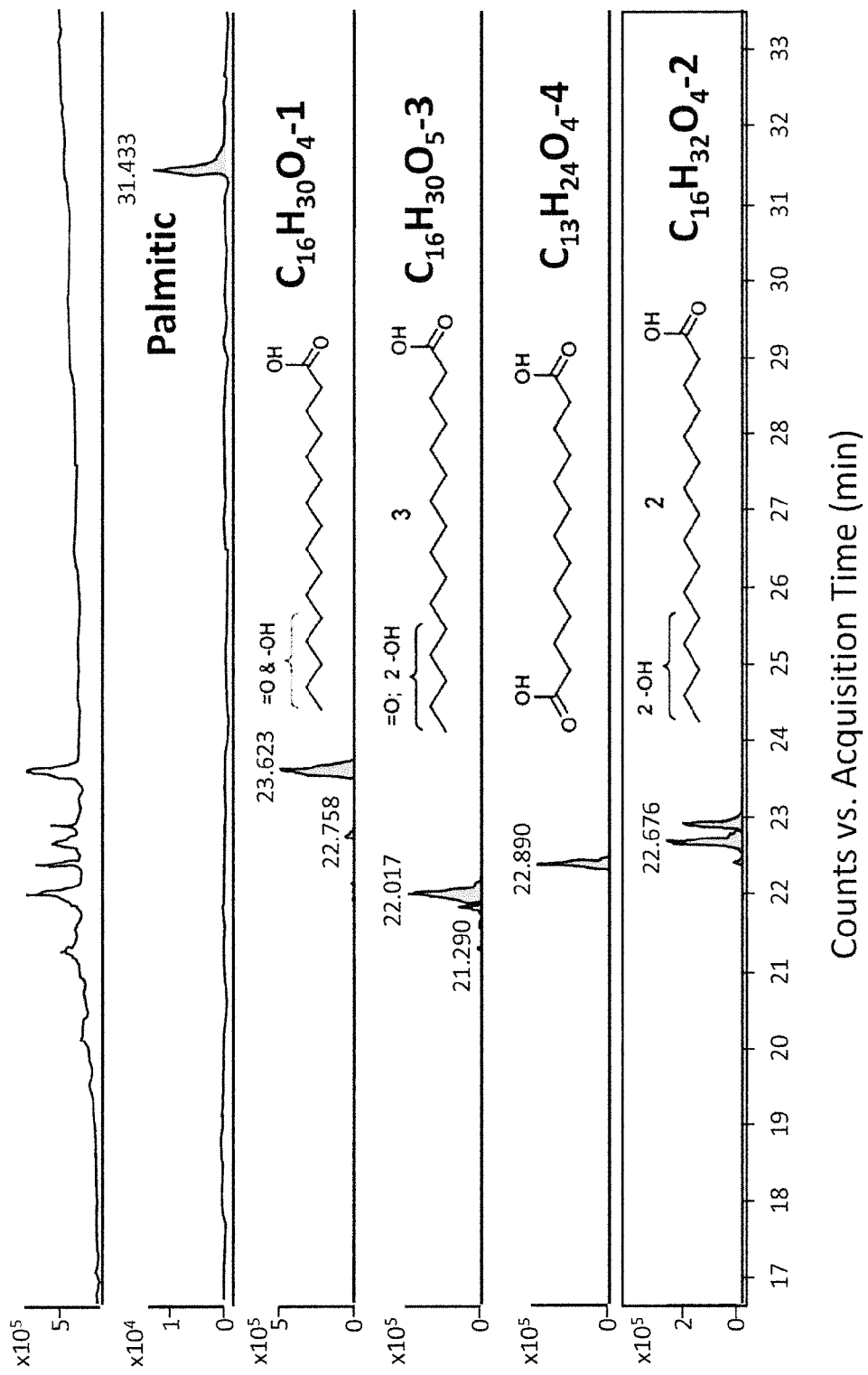
FIG. 10 shows HPLC chromatograms for the oxidation of palmitic acid with BM3-YetO. The top chromatogram shows the total ion count and the remaining show peaks corresponding to different masses and putative species.

The HPLC analysis shows peaks corresponding to various hydroxylation and over-oxidation products, as illustrated in FIG. 10.

Example 3—Oxidation of Cyclic Hydrocarbons

This example illustrates that a mutant CYP102 enzyme (BM3-F87A) oxidizes cyclic hydrocarbons, including cyclooctane and cyclodecane and also produces C—C bond cleavage of cyclodecane. It was found that when the enzyme is placed in the presence of cyclodecane, sebacic acid (decanedioic acid) is produced after over-oxidation.

By performing the reaction in the presence of deuterated lauric acid, we were able to trace the carbons of the produced sebacic acid to the cyclodecane and not the lauric acid. The reaction was thus performed using a mixture of cyclodecane and fully deuterated lauric acid ($C_{12}D_{23}CO_2H$).

Cells of BL21(DE3)/pSGI-004 (pET24a-BM3-F87A) were grown and lysed as described above. A concentration of ~14-20 μM of P450 is obtained under these conditions. Reactions were prepared by mixing 1.5 mL reaction buffer and 0.5 mL of enzyme lysate. Reaction buffer was prepared in 100 mM potassium phosphate (pH 7.8) by adding 4 mM deuterated lauric acid ($C_{12}D_{23}CO_2H$), 1 mM NADP, 1 mg/mL GDH-105 and 50 mM glucose. In this solution cyclodecane dissolved in acetonitrile was added giving a final concentration of 2 mM for cyclodecane and 2% (v/v) for acetonitrile co-solvent. The mixture (1.5 ml) was sonicated for 30 sec to create a milky solution before it was mixed with the enzyme lysate (0.5).

The enzymatic reaction was incubated at 30° C. in a glass test tube with good shaking. After 12 h of incubation 1 mL of the reaction mixture was mixed with 50 uL HCl (3M) and 1 mL of MeOH, centrifuged to remove insoluble proteins and was analyzed by HPLC-MS.

Product analysis revealed various hydroxylated products of the deuterated lauric acid (C12), and a peak that correlates with the same retention time and molecular mass as non-deuterated sebacic acid (C10) (data not shown). Therefore, the carbons of the non-deuterated sebacic acid produced by the reaction had their origin in the cyclodecane, and not the lauric acid (C12). Therefore, the BM3-F87A mutant was able to break the C—C bond of the cyclodecane.

Example 4—Oxidation of Stearic Acid (C18) with a CYP102 Enzyme in a Lysate

Overnight cultures were initiated in 5 mL LB broth from glycerol stocks stored at −80° C. These were grown at 30° C. overnight and 0.5 mL was used to inoculate 50 mL TB broth cultures that were grown at 30° C. to an $OD_{600}$=0.5-1 (3-4 hr) before having 0.25 mM Isopropyl β-D-1-thiogalactopyranoside (IPTG), 0.250 mM δ-aminolevulinic acid (dALA), and 0.50 mM ferric ammonium citrate added for induction. These cultures were grown at 25° C. for 20 h before being centrifuged at 4750×g for 10 min. The supernatant was decanted and the pellets stored at −80° C.

Pellets were resuspended in 5 mL (10% v/v of original culture volume) of 100 mM potassium phosphate, pH 7.8, 10% glycerol, 1 mg/mL lysozyme, 2 U/mL DNase, 1 mM Dithiothreitol (DTT), 5 mM magnesium chloride, and 0.5 mM calcium chloride by vortexing and then shaken at 600 rpm for 1 hr at 37° C. Lysates containing BM3 were then sonicated, centrifuged at 14000×g for 10 min, and decanted. P450 concentrations were calculated using CO binding difference spectra by adding 100 μL lysate to 100 μL 140 mM $Na_2S_2O_4$ and prereading before a 15 min incubation under 10 psi CO. Plates were then read and P450 concentration calculated. Concentrations ranged from 13 nM for BM3 to 2 nM for YetO.

Figure 11:
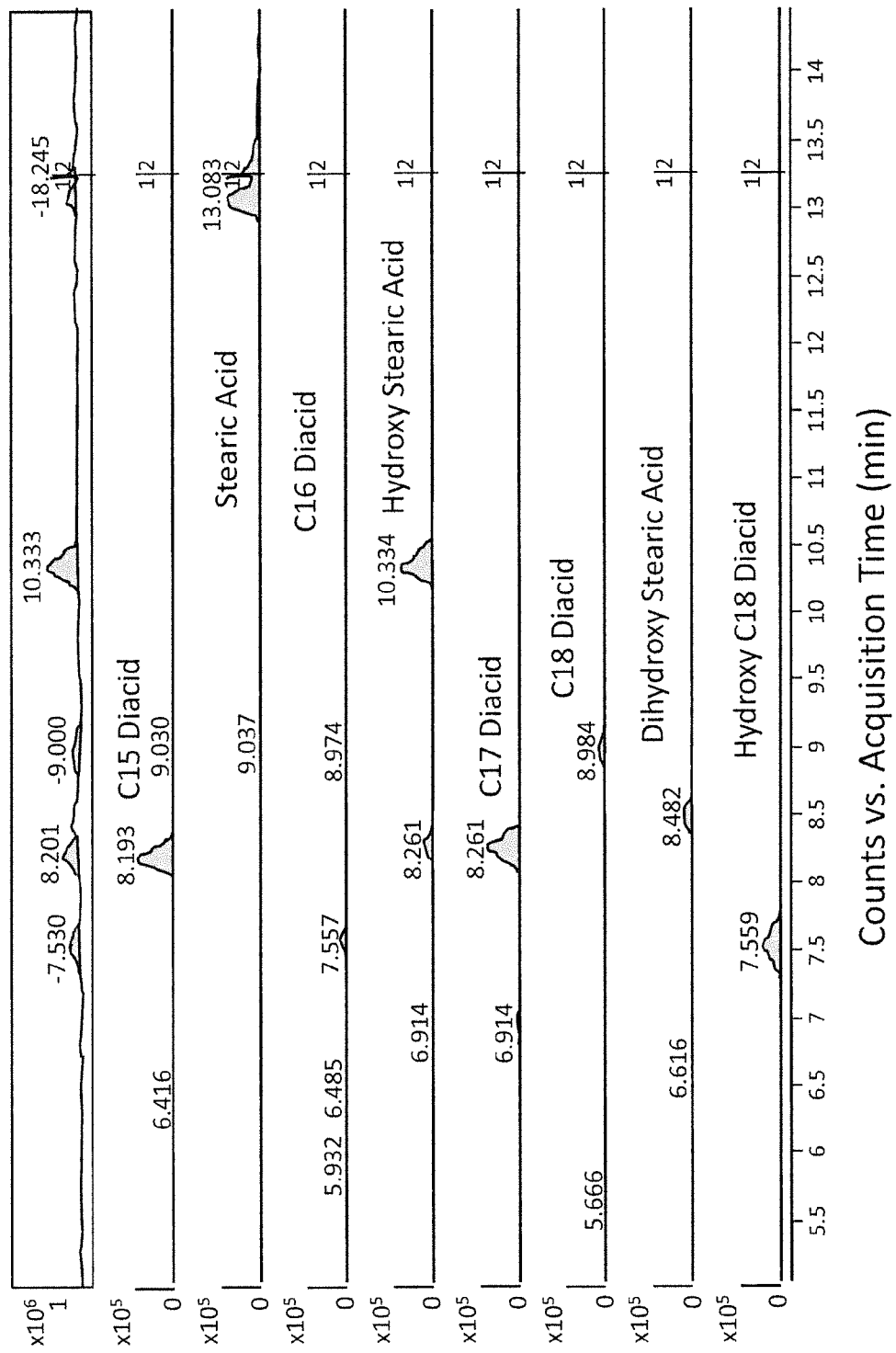
FIG. 11 shows an HPLC chromatogram for the oxidation of stearic acid (C18) with BM3 enzyme in a lysate.

Crude lysates (200 μL) containing each P450 enzyme were mixed with a reaction mixture (800 μL) containing 2 mM stearic acid (C18), 1.0 mM NADPH, 30 mM glucose, and 1 mg/mL glucose dehydrogenase in 100 mM potassium phosphate pH 7.8. After overnight incubation at 30° C. with good shaking, crude reaction mixtures were mixed with 1-5 drops trifluoroacetic acid (TFA) and equal volume tetrahydrofuran (THF). After centrifugation to precipitate the insoluble protein, samples were analyzed by HPLC-MS. A sample chromatogram of a BM3 lysate reaction on stearic acid is shown in FIG. 11. Peaks corresponding to hydroxylation products, including hydroxy stearic acid and dihydroxy stearic acid are clearly visible. Additional peaks for products of the cleavage of a C—C bond are clearly visible, including a C15 (C18-3) dicarboxylic acid and a C17 dicarboxylic acid, are also clearly visible.

Example 5—Oxidation of Heptadecanoic Acid (C17) Using Purified BM3

Overnight cultures were started in 5 mL LB broth from glycerol stocks stored at −80° C. These were grown at 30° C. overnight and used to inoculate 500 mL TB broth cultures that were grown at 30° C. to an $OD_{600}$=0.5-1 (3-4 hr) before having 0.250 mM Isopropyl β-D-1-thiogalactopyranoside (IPTG), 0.250 mM δ-aminolevulinic acid (dALA), and 0.50 mM ferric ammonium citrate added for induction. These cultures were grown at 25° C. for 20 h before being centrifuged at 4750×g for 10 min. The supernatant was decanted and the pellets stored at −80° C.

Pellets were resuspended in 50 mL (10% v/v of original culture volume) of 100 mM potassium phosphate, pH 7.8, 10% glycerol, 1 mg/mL lysozyme, 2 U/mL DNase, 1 mM Dithiothreitol (DTT), 5 mM magnesium chloride, 0.5 mM calcium chloride, 500 mM NaCl and 5 mM imidazole by vortexing and then shaken at 600 rpm for 1 hr at 37° C. Lysates were then sonicated, centrifuged at 14000×g for 10 min, and decanted. Ni-columns were brought to room temperature and centrifuged at 700×g for 2 minutes to remove storage buffer. The 3 mL bed volume columns were then equilibrated with 6 mL of 20 mM Tris HCl, 0.5 M NaCl, 5 mM imidazole and centrifuged at 700×g for 2 minutes. The columns were then filled with lysate and shaken at 160 rpm for 30 min before being centrifuged at 700×g for 2 minutes. This step was repeated until all the lysate had been passed through the columns. The columns were then washed with 6 mL of 20 mM Tris HCl, 0.5 M NaCl, 50 mM imidazole and centrifuged at 700×g for 2 minutes. Three separate elutions were performed with 3 mL of 20 mM Tris HCl, 0.5 M NaCl, 500 mM imidazole and centrifuging at 700×g for 2 minutes. The eluate was then desalted using 10DG desalting columns into 100 mM potassium phosphate pH 7.8. P450 concentrations were calculated using CO binding difference spectra by adding 100 μL purified protein to 100 μL 140 mM $Na_2S_2O_4$ and prereading before a 15 min incubation under 10 PSI CO. Plates were then read and P450 concentration calculated. The concentration of BM3 obtained was 3 nM.

Figure 12:
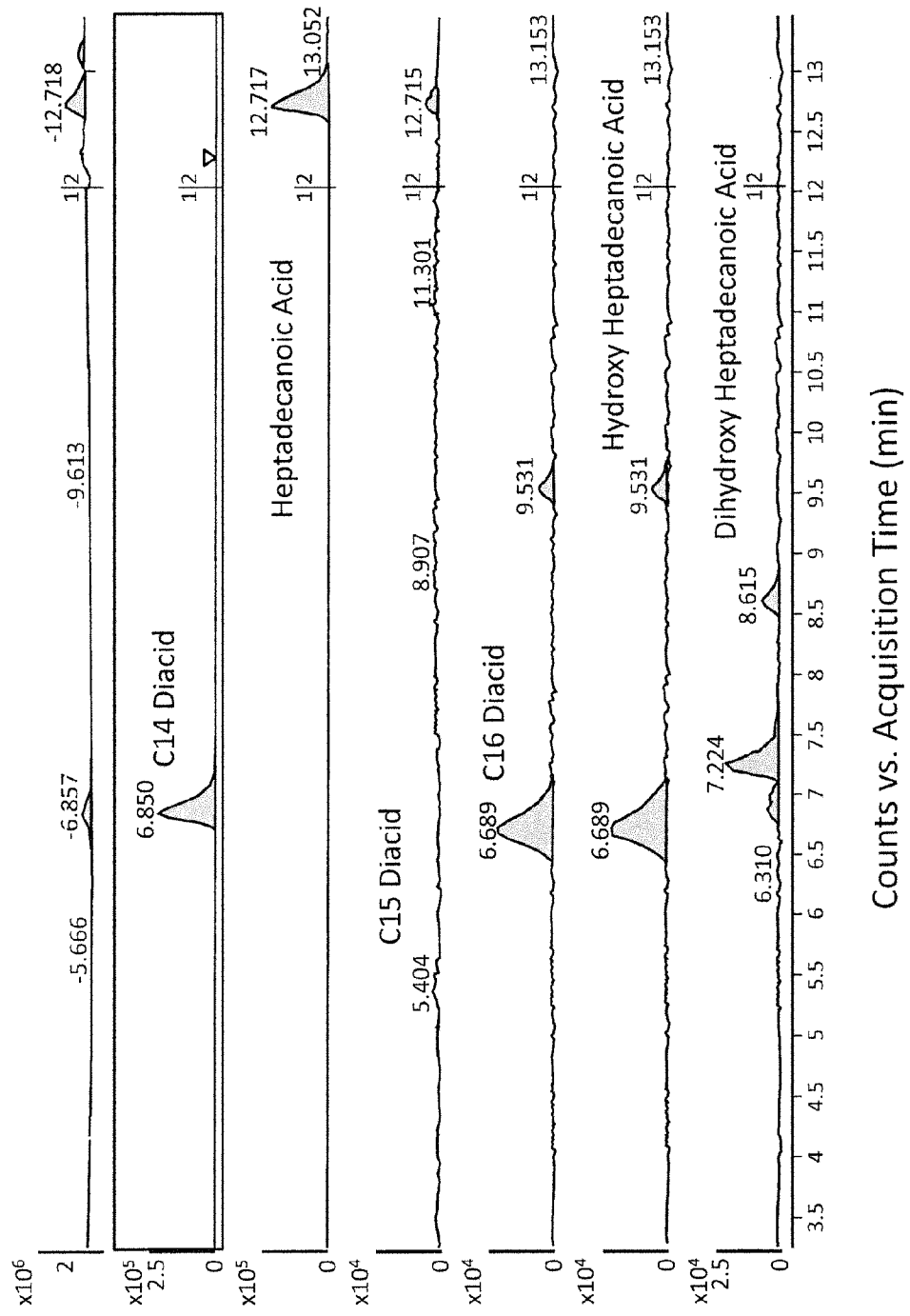
FIG. 12 shows an HPLC chromatogram for the oxidation of heptadecanoic acid (C17) with purified BM3 enzyme.

Purified protein (600 μL) was mixed with a reaction mixture (1400 μL) containing 2 mM heptadecanoic acid (C17), 1.0 mM NADPH, 30 mM glucose, and 1 mg/mL glucose dehydrogenase (GDH-105) in 100 mM potassium phosphate pH 7.8. After overnight incubation at 30° C. with good shaking, crude reaction mixtures were mixed with 1-5 drops trifluoroacetic acid (TFA) and equal volume tetrahydrofuran (THF). After centrifugation to precipitate the insoluble protein, samples were analyzed by HPLC-MS. A sample chromatogram of a BM3 lysate reaction on heptadecanoic acid is shown in FIG. 12. Hydroxylation products of the fatty acid are clearly visible, including hydroxyl heptadecanoic acid and dihydroxy heptadecanoic acid, as well as products of the cleavage of a C—C bond, including C14 dicarboxylic acid (C17-3), C15 dicarboxylic acid, and C16 dicarboxylic acid.

Example 6—Chemical Oxidation of Enzymatic Products with Palmitic Acid

Diols and keto-alcohols and dicarboxylic acids constitute the majority of products from the oxidation of C15-C20 fatty acids with CYP102 enzymes. This example shows that in palmitic acid these diols and keto alcohols are located at the C13 and C14 carbons (□-2 and □-3), and can be converted to C13 di-carboxylic acid upon chemical oxidation as shown in FIG. 7 except that instead of Cyp102 the second step is chemical.

In 1.6 ml of KPi, buffer (50 mM pH 8.0) that contained 2 mM palmitic acid, 50 mM glucose, 1 mg/mL GDH-105, 0.5 mM NADP), 0.4 mL of 5 nM BM3 was added. BM3 enzyme was prepared by 0-60% ammonium sulfate precipitation of crude lysate, and re-dissolving in KPi buffer (50 mM, pH 8.0). After shaking for 16 h at 30° C., 0.2 mL were mixed with 2 drops of TFA, 0.2 mL THF, centrifuged to remove insoluble proteins, and were analyzed by HPLC for product formation (blue bars FIG. 13). Separate samples, 0.4 mL, were removed from the reaction, and were mixed with 8 uL of 30% $H_2O_2$ (w 200 mM final concentration), 1.3 mg of sodium tungstate dihydrate ($Na_2WO_4.2H_2O$, 10 mM final) phosphoric acid to 1 mM to pH-2. This method has been reported to selectively oxidize adjacent diols to the corresponding carboxylic acid by C—C bond breaking (Venturello, C; Ricci, M. *J Org. Chem.* 1986, 51, 1599). After overnight (16 h) incubation at 90° C. the sample was filtered to remove precipitated proteins and was analyzed by HPLC. The results are shown in FIG. 13 (blue bars).

Figure 13:
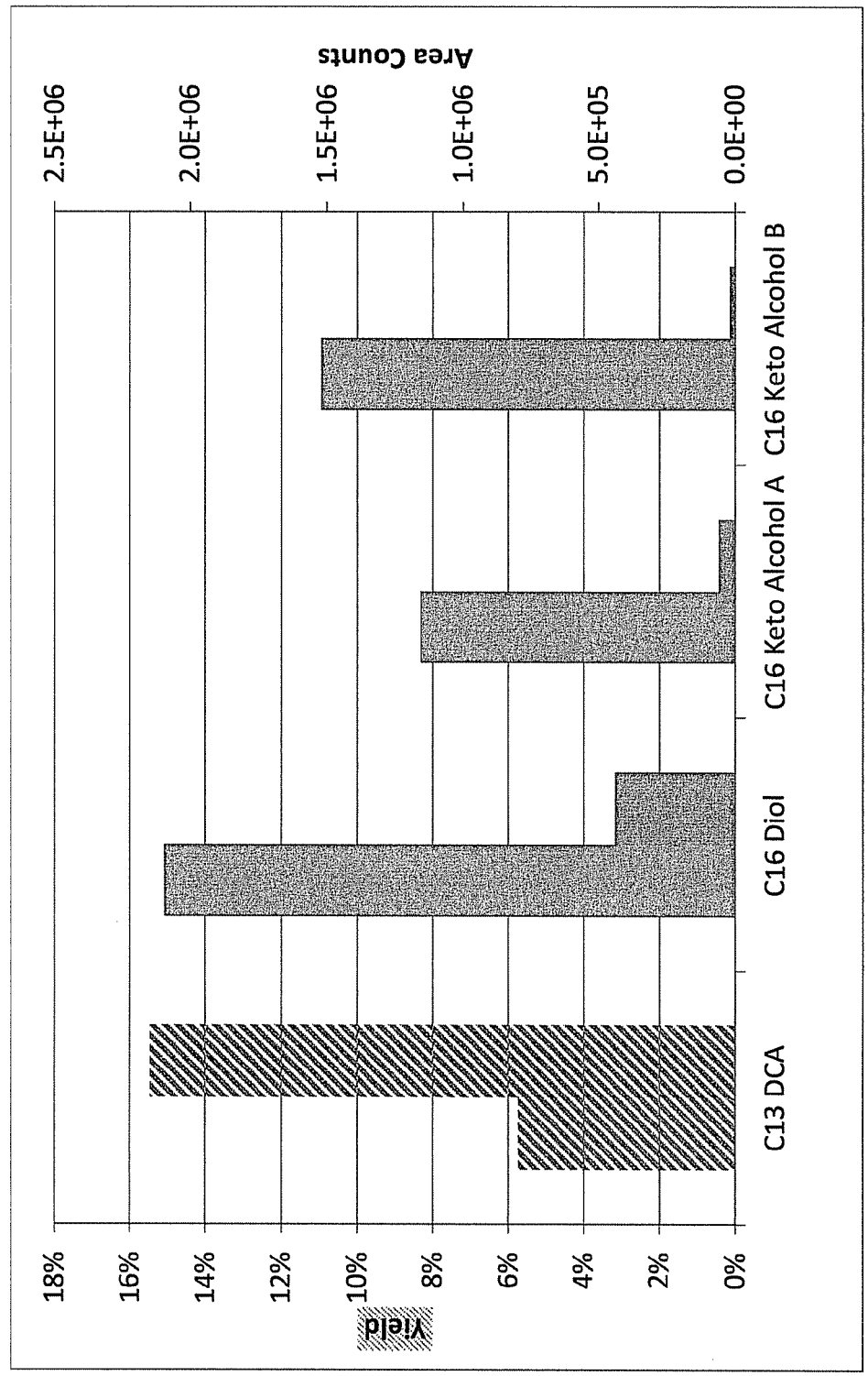
FIG. 13: Concentrations of all major products after the oxidation of palmitic acid with BM3 (left bars) and after chemical treatment (right bars). For tridecanediacid (C13 DCA) the yield to product is shown in the left Y-axis (striped bars); for all other compounds due to the lack of authentic standards, the area count from HPLC analysis is shown (right Y-axis).

As shown in FIG. 13, the enzymatically produced diols and keto alcohols disappeared after chemical treatment with $H_2O_2/Na_2WO_4$. At the same time, the concentration (and associated yield) of C13 di-carboxylic acid increased in the same sample without the accumulation of other HPLC-detectable byproducts. Therefore, the oxidized derivatives are located on C13 and C14 carbons of palmitic acid. BM3 and other enzymes of the CYP102 family stereoselectively produce diols and keto alcohols from saturated fatty acids at ω-2 & ω-3 carbons as shown in FIG. 1. Chemical oxidation of these intermediates produces a single dicarboxylic acid and various chemical conditions and reagents are available for the chemical oxidation step.

The invention claimed is:

1. A method of producing a dicarboxylic acid comprising:
contacting a saturated fatty acid substrate having 15-20 carbon atoms and not bound to or by an acyl carrier protein with a CYP102 sub-family enzyme that comprises a ferredoxin reductase and a ferredoxin and that oxidizes the fatty acid substrate and breaks a C—C bond of the fatty acid substrate to produce a dicarboxylic acid product, wherein the dicarboxylic acid product has 3 less carbon atoms than the substrate and the enzyme has at least 95% sequence identity with a sequence selected from the group consisting of: SEQ ID NOs: 2, 4, 6 and 8; and
detecting the dicarboxylic acid product.

2. The method of claim 1 further comprising that hydroxylated fatty acid products are produced in addition to the dicarboxylic acid product when the enzyme is incubated with the fatty acid.

3. The method of claim 1 wherein the enzyme overoxidizes the fatty acid substrate.

4. The method of claim 3 wherein the reaction comprises the over-oxidation of adjacent diols.

5. The method of claim 1 wherein oxidizing the fatty acid substrate and breaking the C—C bond comprises the reaction mechanism:

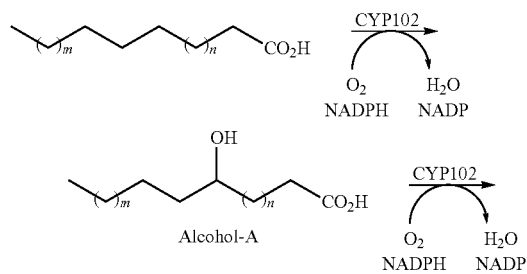

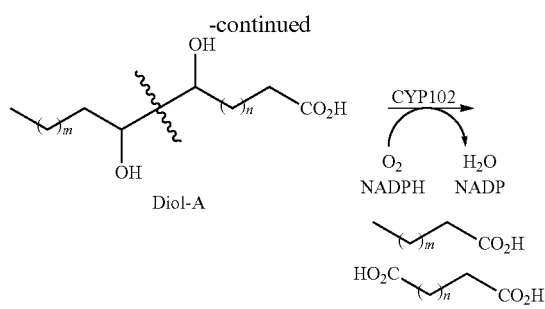

wherein m+n=9-14.

6. The method of claim 5 further comprising contacting the substrate with an oxidizing agent.

7. The method of claim 1 wherein
the substrate is tridecanedioic acid (C19) and the dicarboxylic acid is palmitic acid (C16).

8. The method of claim 1 wherein the enzyme has at least one amino acid residue different from CYP102A1 wt (BM3) and/or CYP102A2 wt (YetO) and/or CYP102A3 wt (yrhJ) enzymes.

9. The method of claim 1 wherein the enzyme is selected from the group consisting of: BM3 (F87A), YetO (F89A), YetO (F89I), YetO (F89S), YetO (F89V).

10. The method of claim 9 wherein the substrate is palmitic acid or heptadecanoic acid.

11. The method of claim 9 wherein the enzyme is BM3-F87A.

12. The method of claim 1 wherein the enzyme has at least one amino acid residue different from CYP102A1 wt (BM3) or CYP102A2 wt (YetO).

13. The method of claim 1 wherein the substrate is palmitic acid or heptadecanoic acid.

14. The method of claim 13 wherein the substrate is palmitic acid.

15. The method of claim 1 wherein the enzyme has the sequence of SEQ ID NO: 2 or SEQ ID NO: 4.

* * * * *

SEQUENCE LISTING

```
<160> NUMBER OF SEQ ID NOS: 8

<210> SEQ ID NO 1
<211> LENGTH: 3150
<212> TYPE: DNA
<213> ORGANISM: Bacillus megaterium

<400> SEQUENCE: 1
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag gagacgggtt atttacaagc tggacgcatg aaaaaaattg gaaaaagcg      300 cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta acagctttta ccgagatcag cctcatccat tattacaag tatggtccgt     540 gcactggatg aagcaatgaa caagctgcag cgagcaaatc cagacgaccc agcttatgat     600
gaaaacaagc gccagtttca agaagatatc aaggtgatga cgacctagt agataaaatt     660 attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgttc caagctacaa acaagtcaaa cagcttaaat atgtcggcat ggtcttaaac     960
```

| | |
|---|---|
| gaagcgctgc gcttatggcc aactgctcct gcgttttccc tatatgcaaa agaagatacg | 1020 |
| gtgcttggag gagaatatcc tttagaaaaa ggcgacgaac taatggttct gattcctcag | 1080 |
| cttcaccgtg ataaaacaat ttggggagac gatgtggaag agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctggata ttaaagaaac tttaacgtta | 1320 |
| aaacctgaag gctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata cgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg cttttatcga tgaaacgctt gccgctaaag gggcagaaaa catcgctgac | 1800 |
| cgcggtgaag cagatgcaag cgacgacttt gaaggcacat atgaagaatg cgtgaacat | 1860 |
| atgtggagtg acgtagcagc ctactttaac ctcgacattg aaaacagtga agataataaa | 1920 |
| tctactcttt cacttcaatt tgtcgacagc gccgcggata tgccgcttgc gaaaatgcac | 1980 |
| ggtgcgtttt caacgaacgt cgtagcaagc aaagaacttc aacagccagg cagtgcacga | 2040 |
| agcacgcgac atcttgaaat tgaacttcca aaagaagctt cttatcaaga aggagatcat | 2100 |
| ttaggtgtta ttcctcgcaa ctatgaagga atagtaaacc gtgtaacagc aaggttcggc | 2160 |
| ctagatgcat cacagcaaat ccgtctggaa gcagaagaag aaaaattagc tcatttgcca | 2220 |
| ctcgctaaaa cagtatccgt agaagagctt ctgcaatacg tggagcttca agatcctgtt | 2280 |
| acgcgcacgc agcttcgcgc aatggctgct aaaacggtct gcccgccgca taaagtagag | 2340 |
| cttgaagcct tgcttgaaaa gcaagcctac aaagaacaag tgctggcaaa acgtttaaca | 2400 |
| atgcttgaac tgcttgaaaa ataccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct tgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg cttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga agaaaaaggc | 3120 |
| cgatacgcaa aagacgtgtg ggctgggtaa | 3150 |

<210> SEQ ID NO 2
<211> LENGTH: 1049
<212> TYPE: PRT

<213> ORGANISM: Bacillus megaterium

<400> SEQUENCE: 2

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400
```

```
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
        610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
    690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
Tyr Val Glu Leu Gln Asp Pro Val Thr Arg Thr Gln Leu Arg Ala Met
            755                 760                 765
Ala Ala Lys Thr Val Cys Pro Pro His Lys Val Glu Leu Glu Ala Leu
    770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
```

```
                820             825              830
Ser Ser Ser Pro Arg Val Asp Glu Lys Gln Ala Ser Ile Thr Val Ser
            835              840             845

Val Val Ser Gly Glu Ala Trp Ser Gly Tyr Gly Glu Tyr Lys Gly Ile
        850              855              860

Ala Ser Asn Tyr Leu Ala Glu Leu Gln Glu Gly Asp Thr Ile Thr Cys
865             870              875                  880

Phe Ile Ser Thr Pro Gln Ser Glu Phe Thr Leu Pro Lys Asp Pro Glu
                885              890              895

Thr Pro Leu Ile Met Val Gly Pro Gly Thr Gly Val Ala Pro Phe Arg
            900             905              910

Gly Phe Val Gln Ala Arg Lys Gln Leu Lys Glu Gln Gly Gln Ser Leu
        915              920              925

Gly Glu Ala His Leu Tyr Phe Gly Cys Arg Ser Pro His Glu Asp Tyr
        930              935              940

Leu Tyr Gln Glu Glu Leu Glu Asn Ala Gln Ser Glu Gly Ile Ile Thr
945             950              955                  960

Leu His Thr Ala Phe Ser Arg Met Pro Asn Gln Pro Lys Thr Tyr Val
                965             970              975

Gln His Val Met Glu Gln Asp Gly Lys Lys Leu Ile Glu Leu Leu Asp
            980             985              990

Gln Gly Ala His Phe Tyr Ile Cys  Gly Asp Gly Ser Gln Met Ala Pro
        995              1000             1005

Ala Val Glu Ala Thr Leu Met  Lys Ser Tyr Ala Asp  Val His Gln
      1010             1015              1020

Val Ser Glu Ala Asp Ala Arg  Leu Trp Leu Gln Gln  Leu Glu Glu
      1025              1030             1035

Lys Gly Arg Tyr Ala Lys Asp  Val Trp Ala Gly
      1040             1045

<210> SEQ ID NO 3
<211> LENGTH: 3183
<212> TYPE: DNA
<213> ORGANISM: Bacillus amyloliquefaciens

<400> SEQUENCE: 3
atgaaggaaa caggtccgat tccgcagccg aagacattcg gcccgctcgg caatcttcct     60
ttgcttgata agacaagcc tacaatgtcg cttatcaaac tggcaaacga gcaggggcct     120 attttcagc tgcatacgcc ggcgggcgcc attatcgtcg tgtccggcca tgaactggtg     180
aaagaggttt gtgatgaaga gcggttcgat aaaagcattg aaggggcttt ggagaaagtc     240
cgggcgtttt ccggtgacgg gctgtttaca agctggacgc atgagcctaa ctggcgaaag     300
gcgcataata ttctgatgcc gaccttcagc cagcgcgcga tgaaagatta tcattcgatg     360
atgactgata tcgcggtgca gctgattcaa aaatgggcta ggctgaaccc ggatgaggcc     420
gttgatgtgc ctgctgatat gacccgcctg acgctcgata cgatcgggct tgcggctttt     480
aactatcggt ttaacagcta ttacagggaa acgcctcatc cgtttatcaa cagcatggtg     540
cgcgcccttg atgaagcgat gcaccaaatg cagcgcttg atgttcagga taagcttatg     600
atcaggacga agcgccaatt tcatcatgac attcaggcga tgttcgtt agtagacagt     660 attattgcag agcgccggtc aggcggccgg gatgaaaagg atctgctggc agaatgctg     720 aatgtggaag acccggaaac gggcgaaaaa cttgatgatg aaaatatccg gtttcaaatc     780
atcacgtttt taattgccgg ccacgaaacg accagcggcc tgctttcctt tgccatctac     840
```

```
tttctgctga acatccccg tgttttggaa aaagcctatg aggaagctga tcgggtattg    900
accgatcccg ttccttcata taaacaagtg ctggatctta cttatatccg aatgattttg    960
caggagtcat tgcgtttatg gccgaccgcg cctgcgttca gcctttatgc gaaagaggat   1020
acggtgatcg gcgggaaata tccgatcacg ccgaaagaca gaatttccgt cttaattccc   1080
cagcttcact gtgataaaga cgcgtgggga gacaatgcgg aggaattttta tccggagcgg   1140
tttgaacatc ctgatcaagt gcctcaccat gcgtataagc cgttcggaaa cggtcagagg   1200
gcgtgtatcg gtatgcagtt cgccctgcat gaagcaactc ttgttctggg gatgattctg   1260
cagcatttta cctttatcga tcacaccgat tatgagctcg atattaaaca gacactgacg   1320
atcaagcccg gcgactttca tatccgggtg cggccgagaa acaagaaagc cgttgcggct   1380
gctctcccgg cggctgaaaa agcggcggaa gacgtcgaaa aagaaaaacg ggaaacaaaa   1440
ggcgcatcca ttatcgggct tgataaccga ccgcttctga ttctgtacgg atcagatacg   1500
ggaaccgcag aaggcgtggc gcgggagctt gccgatactg ccgggatgca cggcgtccgg   1560
actgaaacgg cgcctttaaa tgaccggatc ggaaaactgc cgaaagaagg agctctcttg   1620
atcattacgt cctcttataa cggaaagcct ccgagcaacg cgggacaatt cgttcaatgg   1680
cttgaagaag tcaaacccgg ggaactggaa ggcgtccgat atgccgtctt cggctgcggt   1740
gatcataact gggcggcgac atatcaggct gtaccgaggc ttattgatga aagcttgcc    1800
gaaaaagggg cggaacgctt ttcctcccga ggcgaggggg acgtcagcgg cgattttgaa   1860
ggaaagcttg atgaatggaa aaaaagcatg tggacggacg ccatgaaggc attcggtctc   1920
aagctgaatg aaaatgccga aaagagcga agtgcgctgg gccttcaatt tgtcagcggg   1980
cttggcgggt ctccttttggc acagacgtat gaagcggttt acgcatccgt tgcggaaaac   2040
agggaacttc aggcgccgga aagcggccgg agcacaaggc atatcgaaat cactctgccg   2100
aaagaggctg cctatcatga aggggatcat ctcggcgtgc tgccggtaaa cagcaaagag   2160
caggtcagcc gtgttctccg ccggttcaat ctgaacggga atgatcaagt gctgctgaca   2220
gccagcggac agagcgcggc tcatctcccg ctcgatcggc cggtcaggct gcatgatctt   2280
ctgagcagct gtgtcgaatt gcaggaagcg gcatcaaggg ctcaaatccg ggaaatggcc   2340
gcttatacgg tctgcccgcc gcacaaacgg gaattggaag attttcttga ggagggcgtc   2400
tatcaggagc aaatcttaac atcgcgcgtc tcgatgctcg atctccttga aaatatgaa   2460
gcgtgtgaac ttccgtttga gcgatttctg gagcttttgc gcccgttgaa gccgcggtat   2520
tattcgattt caagttcgcc ccggaaacat cccgggcagg cttcaattac cgtcggcgtc   2580
gttcgcggcc ccgcccggag cggtttgggt gagtatcgcg gagtcgcttc gaattattta   2640
gcggaccgcg gccctgagga tggtatcgtg atgtttgtcc gcactccgga acacgattc    2700
cggctgccgg aagatccgga aaaccgatt attatggtcg gtcccggcac aggagtcgcc   2760
ccgttccgcg gatttctgca agcccgcgcg gcgttaaaaa agaaggaaa agagctgggg   2820
gaggctcatc tgtatttcgg atgcagaaac gatcatgatt ttatttaccg tgacgagctt   2880
gaagcttatg aaaagacgg aatcgtgacg cttcatacgg cttctctccg caaagaaggc   2940
gtaccgaaaa cgtatgtgca gcacttaatg gcgaaagacg ccggcgcttt aatttccatc   3000
ctcggccggg gagggcacct ctacgtatgc ggcgacggca gcaaaatggc gcccgatgta   3060
gaggcaacgc tgcaaaaagc gtatcagtcg gtccacgaaa cagacgaacg gcaagcgcaa   3120
gaatggcttt tggacctcca gacaaaaggc atttacgcaa aagatgtttg gcgggggatt   3180
``` tga 3183

<210> SEQ ID NO 4
<211> LENGTH: 1060
<212> TYPE: PRT
<213> ORGANISM: Bacillus amyloliquefaciens

<400> SEQUENCE: 4

```
Met Lys Glu Thr Gly Pro Ile Pro Gln Pro Lys Thr Phe Gly Pro Leu
1               5                   10                  15

Gly Asn Leu Pro Leu Leu Asp Lys Asp Lys Pro Thr Met Ser Leu Ile
            20                  25                  30

Lys Leu Ala Asn Glu Gln Gly Pro Ile Phe Gln Leu His Thr Pro Ala
        35                  40                  45

Gly Ala Ile Ile Val Val Ser Gly His Glu Leu Val Lys Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Phe Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Ser Met Met Thr Asp Ile Ala Val Gln Leu
        115                 120                 125

Ile Gln Lys Trp Ala Arg Leu Asn Pro Asp Glu Ala Val Asp Val Pro
    130                 135                 140

Ala Asp Met Thr Arg Leu Thr Leu Asp Thr Ile Gly Leu Cys Gly Phe
145                 150                 155                 160

Asn Tyr Arg Phe Asn Ser Tyr Tyr Arg Glu Thr Pro His Pro Phe Ile
                165                 170                 175

Asn Ser Met Val Arg Ala Leu Asp Glu Ala Met His Gln Met Gln Arg
            180                 185                 190

Leu Asp Val Gln Asp Lys Leu Met Ile Arg Thr Lys Arg Gln Phe His
        195                 200                 205

His Asp Ile Gln Ala Met Phe Ser Leu Val Asp Ser Ile Ile Ala Glu
    210                 215                 220

Arg Arg Ser Gly Gly Arg Asp Glu Lys Asp Leu Leu Ala Arg Met Leu
225                 230                 235                 240

Asn Val Glu Asp Pro Glu Thr Gly Glu Lys Leu Asp Asp Glu Asn Ile
                245                 250                 255

Arg Phe Gln Ile Ile Thr Phe Leu Ile Ala Gly His Glu Thr Thr Ser
            260                 265                 270

Gly Leu Leu Ser Phe Ala Ile Tyr Phe Leu Leu Lys His Pro Arg Val
        275                 280                 285

Leu Glu Lys Ala Tyr Glu Glu Ala Asp Arg Val Leu Thr Asp Pro Val
    290                 295                 300

Pro Ser Tyr Lys Gln Val Leu Asp Leu Thr Tyr Ile Arg Met Ile Leu
305                 310                 315                 320

Gln Glu Ser Leu Arg Leu Trp Pro Thr Ala Pro Ala Phe Ser Leu Tyr
                325                 330                 335

Ala Lys Glu Asp Thr Val Ile Gly Gly Lys Tyr Pro Ile Thr Pro Lys
            340                 345                 350

Asp Arg Ile Ser Val Leu Ile Pro Gln Leu His Cys Asp Lys Asp Ala
        355                 360                 365
```

-continued

```
Trp Gly Asp Asn Ala Glu Glu Phe Tyr Pro Glu Arg Phe Glu His Pro
    370                 375                 380
Asp Gln Val Pro His His Ala Tyr Lys Pro Phe Gly Asn Gly Gln Arg
385                 390                 395                 400
Ala Cys Ile Gly Met Gln Phe Ala Leu His Glu Ala Thr Leu Val Leu
                405                 410                 415
Gly Met Ile Leu Gln His Phe Thr Phe Ile Asp His Thr Asp Tyr Glu
            420                 425                 430
Leu Asp Ile Lys Gln Thr Leu Thr Ile Lys Pro Gly Asp Phe His Ile
        435                 440                 445
Arg Val Arg Pro Arg Asn Lys Glu Ala Val Ala Ala Leu Pro Ala
450                 455                 460
Ala Glu Lys Ala Ala Glu Asp Val Glu Lys Lys Arg Glu Thr Lys
465                 470                 475                 480
Gly Ala Ser Ile Ile Gly Leu Asp Asn Arg Pro Leu Ile Leu Tyr
                485                 490                 495
Gly Ser Asp Thr Gly Thr Ala Glu Gly Val Ala Arg Glu Leu Ala Asp
            500                 505                 510
Thr Ala Gly Met His Gly Val Arg Thr Glu Thr Ala Pro Leu Asn Asp
        515                 520                 525
Arg Ile Gly Lys Leu Pro Lys Glu Gly Ala Leu Leu Ile Thr Ser
    530                 535                 540
Ser Tyr Asn Gly Lys Pro Pro Ser Asn Ala Gly Gln Phe Val Gln Trp
545                 550                 555                 560
Leu Glu Glu Val Lys Pro Gly Glu Leu Glu Gly Val Arg Tyr Ala Val
                565                 570                 575
Phe Gly Cys Gly Asp His Asn Trp Ala Ala Thr Tyr Gln Ala Val Pro
            580                 585                 590
Arg Leu Ile Asp Glu Lys Leu Ala Glu Lys Gly Ala Glu Arg Phe Ser
        595                 600                 605
Ser Arg Gly Glu Gly Asp Val Ser Gly Asp Phe Glu Gly Lys Leu Asp
    610                 615                 620
Glu Trp Lys Lys Ser Met Trp Thr Asp Ala Met Lys Ala Phe Gly Leu
625                 630                 635                 640
Lys Leu Asn Glu Asn Ala Glu Lys Glu Arg Ser Ala Leu Gly Leu Gln
                645                 650                 655
Phe Val Ser Gly Leu Gly Gly Ser Pro Leu Ala Gln Thr Tyr Glu Ala
            660                 665                 670
Val Tyr Ala Ser Val Ala Glu Asn Arg Glu Leu Gln Ala Pro Glu Ser
        675                 680                 685
Gly Arg Ser Thr Arg His Ile Glu Ile Thr Leu Pro Lys Glu Ala Ala
    690                 695                 700
Tyr His Glu Gly Asp His Leu Gly Val Leu Pro Val Asn Ser Lys Glu
705                 710                 715                 720
Gln Val Ser Arg Val Leu Arg Arg Phe Asn Leu Asn Gly Asn Asp Gln
                725                 730                 735
Val Leu Leu Thr Ala Ser Gly Gln Ser Ala Ala His Leu Pro Leu Asp
            740                 745                 750
Arg Pro Val Arg Leu His Asp Leu Leu Ser Ser Cys Val Glu Leu Gln
        755                 760                 765
Glu Ala Ala Ser Arg Ala Gln Ile Arg Glu Met Ala Ala Tyr Thr Val
    770                 775                 780
Cys Pro Pro His Lys Arg Glu Leu Glu Asp Phe Leu Glu Glu Gly Val
```

Tyr Gln Glu Gln Ile Leu Thr Ser Arg Val Ser Met Leu Asp Leu Leu
785                 790                 795                 800

Glu Lys Tyr Glu Ala Cys Glu Leu Pro Phe Glu Arg Phe Leu Glu Leu
            805                 810                 815

Leu Arg Pro Leu Lys Pro Arg Tyr Tyr Ser Ile Ser Ser Pro Arg
        820                 825                 830

Lys His Pro Gly Gln Ala Ser Ile Thr Val Gly Val Val Arg Gly Pro
835                 840                 845

Ala Arg Ser Gly Leu Gly Glu Tyr Arg Gly Val Ala Ser Asn Tyr Leu
    850                 855                 860

Ala Asp Arg Gly Pro Glu Asp Gly Ile Val Met Phe Val Arg Thr Pro
865                 870                 875                 880

Glu Thr Arg Phe Arg Leu Pro Glu Asp Pro Lys Pro Ile Ile Met
        885                 890                 895

Val Gly Pro Gly Thr Gly Val Ala Pro Phe Arg Gly Phe Leu Gln Ala
    900                 905                 910

Arg Ala Ala Leu Lys Lys Glu Gly Lys Glu Leu Gly Glu Ala His Leu
        915                 920                 925

Tyr Phe Gly Cys Arg Asn Asp His Asp Phe Ile Tyr Arg Asp Glu Leu
930                 935                 940

945                 950                 955                 960

Glu Ala Tyr Glu Lys Asp Gly Ile Val Thr Leu His Thr Ala Phe Ser
            965                 970                 975

Arg Lys Glu Gly Val Pro Lys Thr Tyr Val Gln His Leu Met Ala Lys
        980                 985                 990

Asp Ala Gly Ala Leu Ile Ser Ile Leu Gly Arg Gly Gly His Leu Tyr
            995                 1000                1005

Val Cys Gly Asp Gly Ser Lys Met Ala Pro Asp Val Glu Ala Thr
    1010                1015                1020

Leu Gln Lys Ala Tyr Gln Ser Val His Glu Thr Asp Glu Arg Gln
    1025                1030                1035

Ala Gln Glu Trp Leu Leu Asp Leu Gln Thr Lys Gly Ile Tyr Ala
    1040                1045                1050

Lys Asp Val Trp Ala Gly Ile
    1055                1060

<210> SEQ ID NO 5
<211> LENGTH: 3240
<212> TYPE: DNA
<213> ORGANISM: Artificial Sequence
<220> FEATURE:
<223> OTHER INFORMATION: Bac0018

<400> SEQUENCE: 5
atgggatatt ttatttcatg ttttttttgaa agggtgtttt taatgaaaaa aaaagtatct      60
gccattcctc aaccgaaaac atatggattg ctggggaatc tcccactaat cgataaagat     120
aaaccgaccc tatcctttat caagatagcg gaagagtatg gtcccatttt tcaaattcaa     180
actttaagtg ataccatcat tgtcgtttct ggacatgaac tggtagcaga agtctgtgac     240
gaaacacggt tcgataaaag tatagagggt gctttagcaa agttcgtgc ctttgctgga     300 gatggattat ttacaagcga gactcaagag cctaactgga aaaagctca taatattttg     360 atgcctacat tcagccaacg agcaatgaaa gattatcatg ctatgatggt cgatattgcc     420
gtacaactcg ttcaaaaatg ggcacggctt aatccgaatg aaaacgtaga tgttccggag     480

```
gatatgactc gccttacatt ggatacaatt ggtctatgtg gttttaatta tcgatttaat    540
agctattatc gtgagacccc tcatccttt attactagca tgagccgtgc tctagatgag    600
gcaatgcacc aattacagcg gctggatata aagataaac tcatgtggag aacgaaacgt    660
caatttcagc atgatattca atctatgttt tctttagtag ataatattat tgctgaacgt    720
aaaagtagtg gaaatcagga agaaaatgat ttactttccc gtatgttaaa tgtgcaggat    780
ccggaaactg gtgaaaaatt agatgatgaa aatattcgtt tccaaattat cactttttta    840
atagctgggc atgaaacaac aagtggatta ttatcttttg caatctattt tttattaaag    900
aatccagata aattgaaaaa agcttatgaa gaagtagatc gggttttaac agatcccact    960
ccaacatacc aacaagttat gaaattaaag tatatccgga tgattttaaa tgaatcgcta   1020
cgtctatggc ctactgctcc agcattcagt ctctatgcaa agaggatac agtgattggt    1080
gggaaatatc ctattaagaa aggagaagat cgtatttctg ttcttattcc acagctacat   1140
agggataaag acgcgtgggg agacaatgtg aagaattcc aacctgaacg atttgaagag   1200
ctggataaga ttccccatca tgcttataag ccatttggaa atggtcaacg agcatgtatc   1260
ggtatgcagt ttgcacttca tgaagccaca ctcgtaatgg gaatgcttct tcaacatttt   1320
gaattcatcg attatcaaga ctatcagctg gacgtaaaaac aaacattaac gctaaagcct   1380
ggtgatttta aaattaggat tctaccccga aacaaaacta ttagccatac tactgttctt   1440
gcgcctatcg aggagaaact gaaaaaccat gaaatcgaac agcaagttca gaaaactcct   1500
tctattattg gagccgataa tctttcgctt cttgttctgt atggatcgga tacaggggta   1560
gcggaaggta ttgcaagaga actagcagat acagctagtt tagaaggtgt tcaaacggaa   1620
gtggtagctc ttaacgatcg aattggaagt ctgccaaaag aaggggcggt tcttattgta   1680
acttcttctt ataatggaaa accaccaagt aatgcagggc agtttgtgca atggttggag   1740
gaattaaaac cggatgagct aaaggtgtt caatacgcag ttttggttg tggagatcat    1800
aattgggcta gtacttatca gcggattcca agatacattg atgagcaaat ggctcaaaaa   1860
ggagcaacaa gattttctac acgtggagaa gcggatgcaa gtggtgattt cgaggaacaa   1920
cttgagcaat ggaaacaaag tatgtggtct gatgcgatga aggcatttgg attggaactt   1980
aacaaaaaca ttgagaaaga acgtagtaca ttaagtttac aatttgttag tcgtcttgga   2040
ggatctcctc ttgcacgaac atatgaagca gtttatgcat ctatactaga aaatcgtgaa   2100
cttcaatcat ctagcagtga aagaagcacg cgacatattg agatatcctt gccagtaggt   2160
gctacgtatc aagaaggtga ccaccttggg gtgctgccaa ttaatagtga gaaaaatgtc   2220
aaccgaattt taaaacgctt tggattaaat gggaaggatc aagtcatatt gagtgcaagt   2280
ggacgaagtg taaatcacat accttttagac agtcctgtta gtttatttga ccttcttagt   2340
tatagtgtag aaattcaaga agcagctact cgagcacaaa tacgagaaat ggtgacattt   2400
acagcatgcc ctcctcataa aaaggaattg gaatcattat tggaagaggg agtttatcat   2460
gaacaaatat taagaaacg tatgtcaatg ttggatcttc ttgaaaagta tgaggcttgt    2520
gaaatccgat ttgaacgctt tttagaactt cttcctgcgc tcaaaccgcg ttactattct   2580
atttcaagct ctccactcgt tgcacaggat cgtctgagca ttacggttgg tgttgttaat   2640
gcacctgcat ggagtggggt agggacatat gaaggagtcg cttctaatta tttagctcag   2700
cgtcataata aagacgagat tatctgtttc attcgaacgc cacaatcaaa ctttcaatta   2760
cctgaaaatc cagaaacacc aattatcatg gttggaccag gtactggaat tgcaccattc   2820
cgtggattct tgcaagcgcg tcgtgttcaa aagcaaaaag gtattaactt aggacaagca   2880
```

```
catctatatt ttggttgtcg tcatcctgaa aaggattatc tctatcgtac agaactagaa    2940
aatgatgaaa gagatggatt aatctcttta cacacagctt tttctcgctt agaaggatat    3000
cctaaaacat atgtacagca tttaataaaa caagatagaa tcaatttaat ttcgttatta    3060
gataatgggg ctcatcttta tatatgtggt gatggaagta aaatggctcc tgacgtagaa    3120
gacacccttt gtcaagcata tcaagaaatt catgaagtca gtgaacaaga agcaaggaat    3180
tggttggatc gtgtgcaaga agaagggcga tatggaaaag atgtttgggc tggtatatga    3240
```

<210> SEQ ID NO 6
<211> LENGTH: 1079
<212> TYPE: PRT
<213> ORGANISM: Artificial Sequence
<220> FEATURE:
<223> OTHER INFORMATION: Bac0018

<400> SEQUENCE: 6

Met Gly Tyr Phe Ile Ser Cys Phe Phe Glu Arg Val Phe Leu Met Glu
1               5                   10                  15

Lys Lys Val Ser Ala Ile Pro Gln Pro Lys Thr Tyr Gly Leu Leu Gly
            20                  25                  30

Asn Leu Pro Leu Ile Asp Lys Asp Lys Pro Thr Leu Ser Phe Ile Lys
        35                  40                  45

Ile Ala Glu Glu Tyr Gly Pro Ile Phe Gln Ile Gln Thr Leu Ser Asp
    50                  55                  60

Thr Ile Ile Val Val Ser Gly His Glu Leu Val Ala Glu Val Cys Asp
65                  70                  75                  80

Glu Thr Arg Phe Asp Lys Ser Ile Glu Gly Ala Leu Ala Lys Val Arg
                85                  90                  95

Ala Phe Ala Gly Asp Gly Leu Phe Thr Ser Thr Gln Glu Pro Asn
            100                 105                 110

Trp Lys Lys Ala His Asn Ile Leu Met Pro Thr Phe Ser Gln Arg Ala
        115                 120                 125

Met Lys Asp Tyr His Ala Met Met Val Asp Ile Ala Val Gln Leu Val
    130                 135                 140

Gln Lys Trp Ala Arg Leu Asn Pro Asn Glu Asn Val Asp Val Pro Glu
145                 150                 155                 160

Asp Met Thr Arg Leu Thr Leu Asp Thr Ile Gly Leu Cys Gly Phe Asn
                165                 170                 175

Tyr Arg Phe Asn Ser Tyr Tyr Arg Glu Thr Pro His Pro Phe Ile Thr
            180                 185                 190

Ser Met Ser Arg Ala Leu Asp Glu Ala Met His Gln Leu Gln Arg Leu
        195                 200                 205

Asp Ile Glu Asp Lys Leu Met Trp Arg Thr Lys Arg Gln Phe Gln His
    210                 215                 220

Asp Ile Gln Ser Met Phe Ser Leu Val Asp Asn Ile Ile Ala Glu Arg
225                 230                 235                 240

Lys Ser Ser Gly Asn Gln Glu Glu Asn Asp Leu Leu Ser Arg Met Leu
                245                 250                 255

Asn Val Gln Asp Pro Glu Thr Gly Glu Lys Leu Asp Asp Glu Asn Ile
            260                 265                 270

Arg Phe Gln Ile Ile Thr Phe Leu Ile Ala Gly His Glu Thr Thr Ser
        275                 280                 285

Gly Leu Leu Ser Phe Ala Ile Tyr Phe Leu Leu Lys Asn Pro Asp Lys
    290                 295                 300

```
Leu Lys Lys Ala Tyr Glu Glu Val Asp Arg Val Leu Thr Asp Pro Thr
305                 310                 315                 320

Pro Thr Tyr Gln Gln Val Met Lys Leu Lys Tyr Ile Arg Met Ile Leu
            325                 330                 335

Asn Glu Ser Leu Arg Leu Trp Pro Thr Ala Pro Ala Phe Ser Leu Tyr
                340                 345                 350

Ala Lys Glu Asp Thr Val Ile Gly Gly Lys Tyr Pro Ile Lys Lys Gly
            355                 360                 365

Glu Asp Arg Ile Ser Val Leu Ile Pro Gln Leu His Arg Asp Lys Asp
        370                 375                 380

Ala Trp Gly Asp Asn Val Glu Glu Phe Gln Pro Glu Arg Phe Glu Glu
385                 390                 395                 400

Leu Asp Lys Ile Pro His His Ala Tyr Lys Pro Phe Gly Asn Gly Gln
                405                 410                 415

Arg Ala Cys Ile Gly Met Gln Phe Ala Leu His Glu Ala Thr Leu Val
            420                 425                 430

Met Gly Met Leu Leu Gln His Phe Glu Phe Ile Asp Tyr Gln Asp Tyr
        435                 440                 445

Gln Leu Asp Val Lys Gln Thr Leu Thr Leu Lys Pro Gly Asp Phe Lys
    450                 455                 460

Ile Arg Ile Leu Pro Arg Lys Gln Thr Ile Ser His Thr Thr Val Leu
465                 470                 475                 480

Ala Pro Ile Glu Glu Lys Leu Lys Asn His Glu Ile Glu Gln Gln Val
                485                 490                 495

Gln Lys Thr Pro Ser Ile Ile Gly Ala Asp Asn Leu Ser Leu Leu Val
            500                 505                 510

Leu Tyr Gly Ser Asp Thr Gly Val Ala Glu Gly Ile Ala Arg Glu Leu
        515                 520                 525

Ala Asp Thr Ala Ser Leu Glu Gly Val Gln Thr Glu Val Val Ala Leu
    530                 535                 540

Asn Asp Arg Ile Gly Ser Leu Pro Lys Glu Gly Ala Val Leu Ile Val
545                 550                 555                 560

Thr Ser Ser Tyr Asn Gly Lys Pro Pro Ser Asn Ala Gly Gln Phe Val
                565                 570                 575

Gln Trp Leu Glu Glu Leu Lys Pro Asp Glu Leu Lys Gly Val Gln Tyr
            580                 585                 590

Ala Val Phe Gly Cys Gly Asp His Asn Trp Ala Ser Thr Tyr Gln Arg
        595                 600                 605

Ile Pro Arg Tyr Ile Asp Glu Gln Met Ala Gln Lys Gly Ala Thr Arg
    610                 615                 620

Phe Ser Thr Arg Gly Glu Ala Asp Ala Ser Gly Asp Phe Glu Glu Gln
625                 630                 635                 640

Leu Glu Gln Trp Lys Gln Ser Met Trp Ser Asp Ala Met Lys Ala Phe
                645                 650                 655

Gly Leu Glu Leu Asn Lys Asn Ile Glu Lys Glu Arg Ser Thr Leu Ser
            660                 665                 670

Leu Gln Phe Val Ser Arg Leu Gly Gly Ser Pro Leu Ala Arg Thr Tyr
        675                 680                 685

Glu Ala Val Tyr Ala Ser Ile Leu Glu Asn Arg Glu Leu Gln Ser Ser
    690                 695                 700

Ser Ser Glu Arg Ser Thr Arg His Ile Glu Ile Ser Leu Pro Val Gly
705                 710                 715                 720
```

-continued

Ala Thr Tyr Gln Glu Gly Asp His Leu Gly Val Leu Pro Ile Asn Ser
                725                 730                 735

Glu Lys Asn Val Asn Arg Ile Leu Lys Arg Phe Gly Leu Asn Gly Lys
            740                 745                 750

Asp Gln Val Ile Leu Ser Ala Ser Gly Arg Ser Val Asn His Ile Pro
        755                 760                 765

Leu Asp Ser Pro Val Ser Leu Phe Asp Leu Leu Ser Tyr Ser Val Glu
    770                 775                 780

Ile Gln Glu Ala Ala Thr Arg Ala Gln Ile Arg Glu Met Val Thr Phe
785                 790                 795                 800

Thr Ala Cys Pro Pro His Lys Lys Glu Leu Glu Ser Leu Leu Glu Glu
                805                 810                 815

Gly Val Tyr His Glu Gln Ile Leu Lys Lys Arg Met Ser Met Leu Asp
            820                 825                 830

Leu Leu Glu Lys Tyr Glu Ala Cys Glu Ile Arg Phe Glu Arg Phe Leu
        835                 840                 845

Glu Leu Leu Pro Ala Leu Lys Pro Arg Tyr Tyr Ser Ile Ser Ser Ser
    850                 855                 860

Pro Leu Val Ala Gln Asp Arg Leu Ser Ile Thr Val Gly Val Val Asn
865                 870                 875                 880

Ala Pro Ala Trp Ser Gly Val Gly Thr Tyr Glu Gly Val Ala Ser Asn
                885                 890                 895

Tyr Leu Ala Gln Arg His Asn Lys Asp Glu Ile Ile Cys Phe Ile Arg
            900                 905                 910

Thr Pro Gln Ser Asn Phe Gln Leu Pro Glu Asn Pro Glu Thr Pro Ile
        915                 920                 925

Ile Met Val Gly Pro Gly Thr Gly Ile Ala Pro Phe Arg Gly Phe Leu
930                 935                 940

Gln Ala Arg Arg Val Gln Lys Gln Lys Gly Ile Asn Leu Gly Gln Ala
945                 950                 955                 960

His Leu Tyr Phe Gly Cys Arg His Pro Gly Lys Asp Tyr Leu Tyr Arg
                965                 970                 975

Thr Glu Leu Glu Asn Asp Glu Arg Asp Gly Leu Ile Ser Leu His Thr
            980                 985                 990

Ala Phe Ser Arg Leu Glu Gly Tyr Pro Lys Thr Tyr Val Gln His Leu
        995                 1000                1005

Ile Lys Gln Asp Arg Ile Asn Leu Ile Ser Leu Leu Asp Asn Gly
    1010                1015                1020

Ala His Leu Tyr Ile Cys Gly Asp Gly Ser Lys Met Ala Pro Asp
    1025                1030                1035

Val Glu Asp Thr Leu Cys Gln Ala Tyr Gln Glu Ile His Glu Val
    1040                1045                1050

Ser Glu Gln Glu Ala Arg Asn Trp Leu Asp Arg Val Gln Glu Glu
    1055                1060                1065

Gly Arg Tyr Gly Lys Asp Val Trp Ala Gly Ile
    1070                1075

<210> SEQ ID NO 7
<211> LENGTH: 3168
<212> TYPE: DNA
<213> ORGANISM: Artificial Sequence
<220> FEATURE:
<223> OTHER INFORMATION: Bac2875

<400> SEQUENCE: 7

```
atgttaatga aacaggcaag cgccatacct cagcccaaaa catacggacc tttaaaaaat    60
cttccgcatc tggaaaaaga gcagctttct caatccttat ggaggttagc tgatgaattg   120
ggaccgattt tccgtttcga ttttccaggg gtgtccagtg tttttgtatc cggacacaat   180
cttgtggctg aagtgtgtga tgaaagccgt tttgacaaaa accttggcaa aggcttgcta   240
aaggtgcgcg agttcggcgg agacggctta tttacaagct ggacccacga accgaactgg   300
caaaaagccc accgcatttt gctgccaagt ttcagtcaaa aagcgatgaa aggctatcat   360
tctatgatgc tggatatcgc aacccagctg attcaaaaat ggagccggct taatcctaat   420
gaagaaattg atgtagcgga cgacatgacc cgtctgacgc ttgatacgat cggattatgc   480
gggtttaact atcgcttcaa cagctttttac cgtgattctc agcatccgtt tatcaccagc   540
atgctcagtg ccttaaaaga ggcgatgaat caatcgaaaa gattgggtct gcaagataag   600
atgatggtga aaacgaagct gcagttccaa aaggatatag aagtcatgaa ctcccttgtc   660
gatagaatga tagcggagcg aaaagagaat ccggatgaaa acattaagga tcttttatcg   720
ctcatgctct atgcaaaaga tcctgtaaca ggtgaaacgc tggatgatga aaatattcga   780
taccaaatca tcacattttt aattgcaggg catgaaacaa caagcggttt gctttccttt   840
gcgatttact gtctgcttac acatccggaa aaactgaaaa aagcgcaaga ggaagccgat   900
cgcgtgttaa cagacacgcc ggaatataaa caaatccagc agctgaaata cattcggatg   960
gtgttaaatg aaacactcag gctatatcca acagctccgg ccttttctct ctatgcgaag  1020
gaggatactg ttctaggcgg ggaatacccg atcagcaaag gtcagcctgt cactgttttg  1080
attccgaagc tgcaccggga tcaaaatgct tggggagaag atgcagaaga ttttcgtccg  1140
gaacggtttg aagacccttc gagtattcct caccatgctt ataagccgtt tggaaacggg  1200
cagcgcgctt gtattggcat gcagtttgct ctccaagaag cgacgatggt tctcggtctt  1260
gtattaaagc attttgattt gatgaaccat actggatacg aactgaaaat caagagggca  1320
ttaacgatca agccggatga atttaaaatt actgtgaaac gcggaaaaac agcagcaatc  1380
aatgtacaga aagagaaca ggctgacaac aaaacagaaa cgaagccaaa agaaacaaaa  1440
cctaaacacg gcacaccttt actcgttctt tacggttcaa accttgggac agcggaagga  1500
atagccggag aattggcagc ttacggccgc cagctgggat ttacagccga acagctccg   1560 cttgatgatt atattggcaa gcttcctgaa caaggcgctg tcgtcatcgt tacggcttct  1620
tataatgggg cgccgcctga taatgctgcc ggctttgtag agtggctgga agagcttgag  1680
gaaggccgat taaaggggt ctcctatgcg gtattcggct gcggaaaccg gagttgggcc  1740
agcacgtatc agcggattcc gcgccttata gatgacatga tgcaagcgaa aggggcatca  1800
cgtttaacac cgattgggga aggtgatgcc gccgatgatt ttgaaagcca tcgcgagtct  1860
tgggaaaacc gcttctggaa ggaatcgata aaagcatttg atataaacga atatctcag   1920 aaagaagaca ggccttcatt atcgattact tttctcagtg aagcgacgga aacgccgctt  1980
gccaaagcat atggtgcgtt tgaagggatt gtcttagaga accgggagct ccagacagct  2040
gatagtccgc gttccacccg ccatattgaa ttgcaggttc ctgacgccaa acatataaaa  2100
gaaggcgatc atatcggaat attgccgaaa acagccagg agcttgttca gcgggttctc  2160
agcagattcg gtttgcagtc caatcatgtg ataaaaatga gcggaagccc tcatatggct  2220
catcttccga tggatcggcc gatcaaagtg gcggatttat tgtcgtccta tgtggagctg  2280
caggaaccgc cttcaaggct tcagcttcgg gagctggctt cttatacagt ttgtccgccg  2340
cataaaaaag agctggaaca gctcgttca gcagatggca tttataaaga gcaggtactg  2400
```

```
gaaaaacgtc tcaccatgct tgatcttttta gaggattacc ctgcctgcga aatgccgttt    2460
gagcggtttt tagaactttt gccttcacta aaaccgcgat attattccat atcaagctca    2520
ccgaaagtgc atgctaatat cgtgagcatg acagtagggg ttgttaaagg ctcagcttgg    2580
agcgggcgcg gagagtaccg gggagtcgcc tctaattatt tagcagagct gaatacaggt    2640
gatgcagcag cctgcttcat ccgaacgccg caatccggat ttcaaatgcc agatgaccct    2700
gaaacgccta tgattatggt cgggccgggt acaggaattg cgccattcag ggctttatt     2760 cagacaagat ctgttttgaa gaaggaagga acacgcttg gtgaagctct tttctatttc    2820
ggctgccggc gccccgatca tgacgatctt tacagagaag agctggatca ggcggaacag    2880
gatggtttgg ttacagtccg ccggtgctat tcacgcgtcg aaaacgaatc aaaagaatat    2940
gtccagcact tgctcaaact agatgcacag aagctgatat cactcattga aaagggggct    3000
cacatttacg tatgcggtga tggatcgcga atggctcctg atgtagagaa tactttgcga    3060
ctggcgtatg aagctgaaaa aggagcaaat caggaagaat cagctgaatg gctgatgaat    3120
ctgcaaaacc aaaaacgcta tgtcaaagac gtttggtcag gtatgtaa                 3168
```

<210> SEQ ID NO 8
<211> LENGTH: 1055
<212> TYPE: PRT
<213> ORGANISM: Artificial Sequence
<220> FEATURE:
<223> OTHER INFORMATION: Bac2875

<400> SEQUENCE: 8

```
Met Leu Met Lys Gln Ala Ser Ala Ile Pro Gln Pro Lys Thr Tyr Gly
1               5                   10                  15

Pro Leu Lys Asn Leu Pro His Leu Glu Lys Glu Gln Leu Ser Gln Ser
            20                  25                  30

Leu Trp Arg Leu Ala Asp Glu Leu Gly Pro Ile Phe Arg Phe Asp Phe
        35                  40                  45

Pro Gly Val Ser Ser Val Phe Val Ser Gly His Asn Leu Val Ala Glu
    50                  55                  60

Val Cys Asp Glu Ser Arg Phe Asp Lys Asn Leu Gly Lys Gly Leu Leu
65                  70                  75                  80

Lys Val Arg Glu Phe Gly Gly Asp Gly Leu Phe Thr Ser Trp Thr His
                85                  90                  95

Glu Pro Asn Trp Gln Lys Ala His Arg Ile Leu Leu Pro Ser Phe Ser
            100                 105                 110

Gln Lys Ala Met Lys Gly Tyr His Ser Met Met Leu Asp Ile Ala Thr
        115                 120                 125

Gln Leu Ile Gln Lys Trp Ser Arg Leu Asn Pro Asn Glu Glu Ile Asp
    130                 135                 140

Val Ala Asp Asp Met Thr Arg Leu Thr Leu Asp Thr Ile Gly Leu Cys
145                 150                 155                 160

Gly Phe Asn Tyr Arg Phe Asn Ser Phe Tyr Arg Asp Ser Gln His Pro
                165                 170                 175

Phe Ile Thr Ser Met Leu Ser Ala Leu Lys Glu Ala Met Asn Gln Ser
            180                 185                 190

Lys Arg Leu Gly Leu Gln Asp Lys Met Met Val Lys Thr Lys Leu Gln
        195                 200                 205

Phe Gln Lys Asp Ile Glu Val Met Asn Ser Leu Val Asp Arg Met Ile
    210                 215                 220

Ala Glu Arg Lys Glu Asn Pro Asp Glu Asn Ile Lys Asp Leu Leu Ser
```

```
            225                 230                 235                 240
Leu Met Leu Tyr Ala Lys Asp Pro Val Thr Gly Glu Thr Leu Asp Asp
                    245                 250                 255
Glu Asn Ile Arg Tyr Gln Ile Ile Thr Phe Leu Ile Ala Gly His Glu
                    260                 265                 270
Thr Thr Ser Gly Leu Leu Ser Phe Ala Ile Tyr Cys Leu Leu Thr His
                    275                 280                 285
Pro Glu Lys Leu Lys Lys Ala Gln Glu Glu Ala Asp Arg Val Leu Thr
                    290                 295                 300
Asp Thr Pro Glu Tyr Lys Gln Ile Gln Gln Leu Lys Tyr Ile Arg Met
305                 310                 315                 320
Val Leu Asn Glu Thr Leu Arg Leu Tyr Pro Thr Ala Pro Ala Phe Ser
                    325                 330                 335
Leu Tyr Ala Lys Glu Asp Thr Val Leu Gly Gly Glu Tyr Pro Ile Ser
                    340                 345                 350
Lys Gly Gln Pro Val Thr Val Leu Ile Pro Lys Leu His Arg Asp Gln
                    355                 360                 365
Asn Ala Trp Gly Glu Asp Ala Glu Asp Phe Arg Pro Glu Arg Phe Glu
                    370                 375                 380
Asp Pro Ser Ser Ile Pro His His Ala Tyr Lys Pro Phe Gly Asn Gly
385                 390                 395                 400
Gln Arg Ala Cys Ile Gly Met Gln Phe Ala Leu Gln Glu Ala Thr Met
                    405                 410                 415
Val Leu Gly Leu Val Leu Lys His Phe Asp Leu Met Asn His Thr Gly
                    420                 425                 430
Tyr Glu Leu Lys Ile Lys Glu Ala Leu Thr Ile Lys Pro Asp Glu Phe
                    435                 440                 445
Lys Ile Thr Val Lys Pro Arg Lys Thr Ala Ala Ile Asn Val Gln Arg
                    450                 455                 460
Arg Glu Gln Ala Asp Asn Lys Thr Glu Thr Lys Pro Lys Glu Thr Lys
465                 470                 475                 480
Pro Lys His Gly Thr Pro Leu Leu Val Leu Tyr Gly Ser Asn Leu Gly
                    485                 490                 495
Thr Ala Glu Gly Ile Ala Gly Glu Leu Ala Ala Tyr Gly Arg Gln Leu
                    500                 505                 510
Gly Phe Thr Ala Glu Thr Ala Pro Leu Asp Asp Tyr Ile Gly Lys Leu
                    515                 520                 525
Pro Glu Gln Gly Ala Val Val Ile Val Thr Ala Ser Tyr Asn Gly Ala
                    530                 535                 540
Pro Pro Asp Asn Ala Ala Gly Phe Val Glu Trp Leu Glu Glu Leu Glu
545                 550                 555                 560
Glu Gly Arg Leu Lys Gly Val Ser Tyr Ala Val Phe Gly Cys Gly Asn
                    565                 570                 575
Arg Ser Trp Ala Ser Thr Tyr Gln Arg Ile Pro Arg Leu Ile Asp Asp
                    580                 585                 590
Met Met Gln Ala Lys Gly Ala Ser Arg Leu Thr Pro Ile Gly Glu Gly
                    595                 600                 605
Asp Ala Ala Asp Phe Glu Ser His Arg Glu Ser Trp Glu Asn Arg
                    610                 615                 620
Phe Trp Lys Glu Ser Ile Lys Ala Phe Asp Ile Asn Glu Ile Ser Gln
625                 630                 635                 640
Lys Glu Asp Arg Pro Ser Leu Ser Ile Thr Phe Leu Ser Glu Ala Thr
                    645                 650                 655
```

-continued

Glu Thr Pro Leu Ala Lys Ala Tyr Gly Ala Phe Glu Gly Ile Val Leu
        660                 665                 670

Glu Asn Arg Glu Leu Gln Thr Ala Asp Ser Pro Arg Ser Thr Arg His
        675                 680                 685

Ile Glu Leu Gln Val Pro Asp Ala Lys Thr Tyr Lys Glu Gly Asp His
690                 695                 700

Ile Gly Ile Leu Pro Lys Asn Ser Gln Glu Leu Val Gln Arg Val Leu
705                 710                 715                 720

Ser Arg Phe Gly Leu Gln Ser Asn His Val Ile Lys Met Gly Ser
                725                 730                 735

Pro His Met Ala His Leu Pro Met Asp Arg Pro Ile Lys Val Ala Asp
        740                 745                 750

Leu Leu Ser Ser Tyr Val Glu Leu Gln Glu Pro Ala Ser Arg Leu Gln
        755                 760                 765

Leu Arg Glu Leu Ala Ser Tyr Thr Val Cys Pro Pro His Lys Lys Glu
        770                 775                 780

Leu Glu Gln Leu Val Ser Ala Asp Gly Ile Tyr Lys Glu Gln Val Leu
785                 790                 795                 800

Glu Lys Arg Leu Thr Met Leu Asp Leu Leu Glu Asp Tyr Pro Ala Cys
                805                 810                 815

Glu Met Pro Phe Glu Arg Phe Leu Glu Leu Leu Pro Ser Leu Lys Pro
                820                 825                 830

Arg Tyr Tyr Ser Ile Ser Ser Ser Pro Lys Val His Ala Asn Ile Val
        835                 840                 845

Ser Met Thr Val Gly Val Val Lys Gly Ser Ala Trp Ser Gly Arg Gly
        850                 855                 860

Glu Tyr Arg Gly Val Ala Ser Asn Tyr Leu Ala Glu Leu Asn Thr Gly
865                 870                 875                 880

Asp Ala Ala Ala Cys Phe Ile Arg Thr Pro Gln Ser Gly Phe Gln Met
                885                 890                 895

Pro Asp Asp Pro Glu Thr Pro Met Ile Met Val Gly Pro Gly Thr Gly
        900                 905                 910

Ile Ala Pro Phe Arg Gly Phe Ile Gln Thr Arg Ser Val Leu Lys Lys
        915                 920                 925

Glu Gly Asn Thr Leu Gly Glu Ala Leu Phe Tyr Phe Gly Cys Arg Arg
930                 935                 940

Pro Asp His Asp Asp Leu Tyr Arg Glu Glu Leu Asp Gln Ala Glu Gln
945                 950                 955                 960

Asp Gly Leu Val Thr Val Arg Arg Cys Tyr Ser Arg Val Glu Asn Glu
                965                 970                 975

Ser Lys Glu Tyr Val Gln His Leu Leu Lys Leu Asp Ala Gln Lys Leu
        980                 985                 990

Ile Ser Leu Ile Glu Lys Gly Ala His Ile Tyr Val Cys Gly Asp Gly
        995                 1000                1005

Ser Arg Met Ala Pro Asp Val Glu Asn Thr Leu Arg Leu Ala Tyr
        1010                1015                1020

Glu Ala Glu Lys Gly Ala Asn Gln Glu Glu Ser Ala Glu Trp Leu
        1025                1030                1035

Met Asn Leu Gln Asn Gln Lys Arg Tyr Val Lys Asp Val Trp Ser
        1040                1045                1050

Gly Met
1055